United States Patent
Sharma et al.

(10) Patent No.: US 11,318,314 B2
(45) Date of Patent: May 3, 2022

(54) DELIVERY OF CARDIAC PACING THERAPY FOR CARDIAC REMODELING

(71) Applicant: Medtronic, Inc., Minneapolis, MN (US)

(72) Inventors: Vinod Sharma, Maple Grove, MN (US); Teresa A. Whitman, Dayton, MN (US); Troy E. Jackson, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 55 days.

(21) Appl. No.: 16/441,738

(22) Filed: Jun. 14, 2019

(65) Prior Publication Data

US 2019/0381322 A1 Dec. 19, 2019

Related U.S. Application Data

(60) Provisional application No. 62/684,828, filed on Jun. 14, 2018.

(51) Int. Cl.
*A61N 1/365* (2006.01)
*A61N 1/362* (2006.01)
(Continued)

(52) U.S. Cl.
CPC ....... *A61N 1/36592* (2013.01); *A61N 1/3627* (2013.01); *A61N 1/36521* (2013.01); *A61N 1/3684* (2013.01); *A61N 1/36114* (2013.01)

(58) Field of Classification Search
CPC .............. A61N 1/36592; A61N 1/3627; A61N 1/36521; A61N 1/36114; A61N 1/362;
(Continued)

(56) References Cited

U.S. PATENT DOCUMENTS 4,428,378 A 1/1984 Anderson et al.
4,567,892 A * 2/1986 Plicchi ................. A61B 5/0809
607/20
(Continued)

FOREIGN PATENT DOCUMENTS

EP 2809393 B1 * 11/2016 ......... A61B 5/14503
WO WO 2005/039690 A1 5/2005
(Continued)

OTHER PUBLICATIONS

Boehmer et al. A Multisensor Algorithm Predicts Heart Failure Events in Patients With Implanted Devices: Results From the MultiSENSE Study, JACC: Heart Failure, vol. 5, Issue 3, 2017, pp. 216-225, ISSN 2213-1779 (Year: 2017).*
(Continued)

*Primary Examiner* — Carl H Layno
*Assistant Examiner* — Manolis Pahakis
(74) *Attorney, Agent, or Firm* — Mueting Raasch Group

(57) ABSTRACT

A method and device apparatus to deliver a pacing therapy capable of remodeling a patient's heart over a period of time that includes monitoring one or more parameters in response to a delivered cardiac remodeling pacing, determining whether the cardiac remodeling pacing has an effect on cardiac normalization in response to the monitoring, and adjusting the cardiac remodeling pacing in response to the determined effect on cardiac normalization. The method and device may also perform short-term monitoring of one or more parameters in response to the delivered cardiac remodeling pacing, monitor one or more long-term parameter indicative of a long-term effect of the delivered cardiac remodeling pacing, determine the long-term effect of the delivered cardiac remodeling pacing on cardiac normalization in response to the monitoring, and adjust the cardiac remodeling pacing in response to one or both of the short-
(Continued)

term monitoring and the determined long-term effect on cardiac normalization.

16 Claims, 9 Drawing Sheets

(51) Int. Cl.
*A61N 1/36* (2006.01)
*A61N 1/368* (2006.01)

(58) Field of Classification Search
CPC .... A61N 1/3684; A61N 1/3702; A61N 1/365; A61N 1/371; A61N 1/059; G16H 50/20; A61B 5/686; A61B 5/1118; A61B 5/7246; A61B 5/04525; A61B 5/0472; A61B 5/021; A61B 5/026; A61B 3/1233; A61B 3/1241; A61M 16/024
See application file for complete search history.

(56) References Cited

U.S. PATENT DOCUMENTS

| | | | |
|---|---|---|---|
| 4,644,954 A * | 2/1987 | Wittkampf | A61N 1/365 607/25 |
| 4,867,161 A * | 9/1989 | Schaldach | A61N 1/36585 607/17 |
| 4,884,576 A * | 12/1989 | Alt | A61N 1/36521 607/18 |
| 5,052,388 A | 10/1991 | Sivula et al. | |
| 5,052,454 A | 10/1991 | Meinhardt | |
| 5,097,831 A * | 3/1992 | Lekholm | A61N 1/3704 607/18 |
| 5,197,467 A * | 3/1993 | Steinhaus | A61N 1/36521 600/547 |
| 5,292,340 A * | 3/1994 | Crosby | A61N 1/36521 607/17 |
| 5,318,597 A * | 6/1994 | Hauck | A61N 1/36521 607/20 |
| 5,876,353 A * | 3/1999 | Riff | A61B 5/0809 600/547 |
| 6,298,268 B1 * | 10/2001 | Ben-Haim | A61N 1/3627 607/9 |
| 6,314,322 B1 * | 11/2001 | Rosenberg | A61N 1/36514 607/17 |
| 6,650,937 B2 | 11/2003 | Kerver | |
| 7,133,718 B2 | 11/2006 | Bakken et al. | |
| 7,194,306 B1 * | 3/2007 | Turcott | A61N 1/36514 607/17 |
| 7,305,266 B1 * | 12/2007 | Kroll | A61N 1/37512 607/28 |
| 7,445,605 B2 * | 11/2008 | Overall | A61B 5/02444 600/483 |
| 7,630,078 B1 * | 12/2009 | Nabutovsky | A61B 5/02028 356/392 |
| 7,660,616 B1 * | 2/2010 | Poore | A61B 5/1459 600/341 |
| 7,840,246 B1 * | 11/2010 | Poore | A61B 5/14535 600/339 |
| 7,941,216 B2 * | 5/2011 | Salo | A61N 1/36842 607/9 |
| 8,027,724 B2 | 9/2011 | Wei et al. | |
| 8,046,069 B2 * | 10/2011 | Kramer | A61B 5/6826 607/23 |
| 8,126,549 B2 * | 2/2012 | Sigg | A61N 1/365 607/9 |
| 8,306,615 B2 * | 11/2012 | Brockway | A61N 1/36585 607/6 |
| 8,386,038 B2 | 2/2013 | Bianchi et al. | |
| 8,600,497 B1 * | 12/2013 | Yang | A61B 5/02028 607/7 |
| 8,798,751 B2 * | 8/2014 | Spear | A61N 1/37 607/27 |
| 9,002,454 B2 | 4/2015 | Ghosh et al. | |
| 9,320,906 B2 * | 4/2016 | Maskara | A61N 1/371 |
| 9,403,016 B2 * | 8/2016 | Meyer | A61N 1/365 |
| 9,956,416 B2 | 5/2018 | Ghosh et al. | |
| 10,029,103 B2 | 7/2018 | Sweeney | |
| 10,702,698 B2 | 7/2020 | Zhao et al. | |
| 2003/0158584 A1 * | 8/2003 | Cates | A61B 5/076 607/2 |
| 2004/0199210 A1 * | 10/2004 | Shelchuk | A61N 1/36114 607/17 |
| 2006/0100668 A1 * | 5/2006 | Ben-David | A61N 1/36114 607/2 |
| 2006/0178586 A1 * | 8/2006 | Dobak | A61B 5/352 600/508 |
| 2006/0224196 A1 * | 10/2006 | Hettrick | A61N 1/3627 607/9 |
| 2006/0224203 A1 * | 10/2006 | Hettrick | A61N 1/3627 607/19 |
| 2006/0247692 A1 * | 11/2006 | Yang | A61N 1/36564 607/9 |
| 2007/0150017 A1 * | 6/2007 | Salo | A61N 1/3627 607/22 |
| 2007/0203522 A1 * | 8/2007 | Hettrick | A61N 1/3627 607/9 |
| 2008/0051840 A1 * | 2/2008 | Moaddeb | A61N 1/3627 607/3 |
| 2008/0114408 A1 * | 5/2008 | Shuros | A61N 1/3684 607/11 |
| 2008/0119898 A1 * | 5/2008 | Ben-David | A61N 1/36114 607/2 |
| 2008/0132800 A1 * | 6/2008 | Hettrick | A61B 5/076 600/509 |
| 2008/0188721 A1 * | 8/2008 | Patangay | A61B 7/00 600/301 |
| 2008/0234776 A1 * | 9/2008 | KenKnight | A61N 1/3627 607/19 |
| 2009/0005831 A1 * | 1/2009 | Wilson | A61N 1/3627 607/27 |
| 2009/0093857 A1 * | 4/2009 | Markowitz | A61N 1/05 607/11 |
| 2009/0234401 A1 * | 9/2009 | Zielinski | A61N 1/368 607/4 |
| 2010/0016923 A1 * | 1/2010 | Rousso | C12N 13/00 607/59 |
| 2010/0082077 A1 * | 4/2010 | Bruns | A61N 1/36564 607/18 |
| 2010/0087887 A1 | 4/2010 | Dong et al. | |
| 2010/0152802 A1 * | 6/2010 | Min | A61N 1/368 607/14 |
| 2010/0152804 A1 * | 6/2010 | Kleckner | A61N 1/36114 607/17 |
| 2012/0010674 A1 * | 1/2012 | Pastore | A61N 1/36842 607/9 |
| 2012/0035679 A1 * | 2/2012 | Dagan | A61N 1/0553 607/14 |
| 2012/0101541 A1 * | 4/2012 | Corbucci | A61N 1/3925 607/17 |
| 2012/0150252 A1 * | 6/2012 | Feldman | A61N 1/36843 607/18 |
| 2012/0303078 A1 * | 11/2012 | Li | A61N 1/36585 607/4 |
| 2012/0323099 A1 | 12/2012 | Mothilal et al. | |
| 2013/0237873 A1 * | 9/2013 | Zhang | A61B 5/6869 600/513 |
| 2014/0100621 A1 * | 4/2014 | Feldman | A61B 5/02028 607/4 |
| 2014/0277237 A1 * | 9/2014 | Maskara | A61N 1/0492 607/18 |
| 2015/0250428 A1 * | 9/2015 | Zhang | A61B 5/7275 600/301 |
| 2016/0361559 A1 * | 12/2016 | Scharmer | A61N 1/36014 |
| 2017/0079598 A1 * | 3/2017 | Stolen | A61B 5/02405 |
| 2017/0290550 A1 * | 10/2017 | Perschbacher | A61B 5/0468 |
| 2018/0126171 A1 | 5/2018 | Herrmann et al. | |
| 2019/0167972 A1 * | 6/2019 | Stahmann | A61N 1/059 |
| 2019/0167991 A1 * | 6/2019 | Stahmann | A61N 1/36514 |

(56) References Cited

U.S. PATENT DOCUMENTS

| | | | |
|---|---|---|---|
| 2019/0168007 A1* | 6/2019 | Stahmann | A61N 1/36167 |
| 2019/0201696 A1* | 7/2019 | Koop | A61N 1/3706 |
| 2019/0336096 A1* | 11/2019 | Itu | G06N 3/08 |
| 2020/0038663 A1 | 2/2020 | Meyer | |
| 2020/0289829 A1* | 9/2020 | Ghosh | A61N 1/368 |

FOREIGN PATENT DOCUMENTS

| | | |
|---|---|---|
| WO | WO 2005/118062 A2 | 12/2005 |
| WO | 2008/109040 | 9/2008 |
| WO | 2013/010165 | 1/2013 |
| WO | WO 2018/067931 A1 | 4/2018 |

OTHER PUBLICATIONS

Effect of Cardiac Resynchronization Therapy on Reverse Remodeling and Relation to Outcome Solomon et al. American Heart Association. vol. 122, Issue 10, Sep. 7, 2010, pp. 985-992 (Year: 2010).*

U.S. Appl. No. 62/573,685, filed Oct. 17, 2018, Zhou.
U.S. Appl. No. 62/581,486, filed Nov. 3, 2018, Zhou.
Westermann et al., "Role of left ventricular stiffness in heart failure with normal ejection fraction," *Circulation*, Apr. 22, 2008: 117 (16):2051-60.
Jarvelainen et al., "Extracellular Matrix Molecules: Potential Targets in Pharmacotherapy," *Pharmacol Rev*, 2009, 61:198-223.
International Search Report and Written Opinion dated Jan. 16, 2020, for International Application No. PCT/US2019/037229; 21 pages.
Gimelli et al., "CRT in Patients with Heart Failure: Time Course of Perfusion and Wall Motion Changes," 2010, *Cardiology Research and Practice*, 2010:981064, 5 pages.
International Search Report and Written Opinion dated Oct. 4, 2019, for International Application No. PCT/US2019/037253; 15 pages.
Partial International Search and Provisional Opinion dated Nov. 13, 2019, for International Application No. PCT/US2019/037229, 18 pages.
Office action from U.S. Appl. No. 16/441,764 dated Feb. 2, 2021, 22 pages.

* cited by examiner

DELIVERY OF CARDIAC PACING THERAPY FOR CARDIAC REMODELING

RELATED APPLICATION

This application claims the benefit of U.S. Provisional Application No. 62/684,828, filed Jun. 14, 2018, the disclosure of which is incorporated by reference herein in its entirety.

FIELD

The present disclosure pertains to cardiac pacing methods and systems, and, more particularly, to a method and apparatus for delivering cardiac remodeling pacing in an implantable medical device.

BACKGROUND

Heart failure (HF) is a complex disease state broadly defined by an inability of the heart to pump sufficiently to cope with its venous return and/or to deliver sufficient output to meet the metabolic demands of the body. Heart failure is an increasingly common, life-threatening cardiovascular disorder, characterized by marked disability, frequent hospitalization and high mortality. HF is increasingly prevalent in older individuals (up to 10% of the population) and it has become the most common cause for hospitalization in people>65 yrs. HF is a leading cause or contributor to hospitalization and therefore is emerging as a substantial contributor to healthcare spending. The particular clinical manifestations of HF are determined by the underlying cause of the heart failure.

The term heart failure (HF) refers broadly to a pathophysiologic disorder in which cardiac performance is incapable of delivering sufficient blood to meet metabolic demand (e.g. during physical activity or in severe cases at rest), or to accommodate venous return. A range of further sub-classifications and/or structure of the heart, can then be applied, based on the symptoms exhibited by the patient. Exemplary classifications of heart failure by symptoms or objective assessments are provided by the New York Heart Association (classes I-IV, classes A-D)). Heart failure can also be defined by ejection fraction. Generally, patients exhibiting an ejection fraction of less than or equal to 0.35 are classified as having heart failure with reduced ejection fraction (HFrEF) while an ejection fraction above 0.35 is considered to be heart failure with preserved ejection fraction (HFpEF).

Congestive heart failure symptoms are indicative of congestive heart failure. Exemplary congestive heart failure symptoms include reduced cardiac output leading to easy fatigue and organ dysfunction (e.g. renal), and to symptoms related to congestion either in the lungs (causing breathlessness) or peripherally (leading to swelling of the lower limbs and abdomen).

A possible correlation has been identified between sedentary lifestyle and risk of ventricular arrhythmias based on a comparison of occurrences of ventricular arrhythmias in healthy active vs. sedentary men, and men with previous myocardial infarction. One result of a sedentary lifestyle is that the size of the chambers of the heart may decrease, which often occurs as a result of increased muscle thickness. Accordingly, the greatest number and highest grades of ventricular arrhythmias during exercise were found in healthy sedentary men.

Nearly half of all patients with heart failure have a normal ejection fraction (EF), commonly referred to as heart failure with preserved ejection fraction (HFpEF). In congestive heart failure patients with HFpEF the amount of blood pumped from the heart's left ventricle with each beat (ejection fraction) is greater than 50%. HFpEF is also commonly known as diastolic heart failure or diastolic dysfunction, as the deficit in function frequently relates to changes occurring during diastole and filling of the ventricles. Approximately half of people with heart failure have HFpEF, while the remainder display a reduction in ejection fraction, or heart failure with reduced ejection fraction (HFrEF).

The prevalence of HFpEF continues to increase, likely because of the increasing prevalence of common risk factors, including older age, hypertension, metabolic syndrome, renal dysfunction and obesity. HFpEF is characterized by abnormal diastolic function, which manifests as an increase in the stiffness of the heart's left ventricle, a decrease in left ventricular relaxation when filling with blood before the next beat, and decreased chamber volume, which often occurs as a result of increased muscle thickness. There is an increased risk for atrial fibrillation and pulmonary hypertension for patient's experiencing HFpEF.

SUMMARY

The present disclosure is directed to a method and device for delivering a pacing therapy capable of remodeling a patient's heart over a period of time. According to one example of the present disclosure, a method comprises delivering cardiac remodeling pacing to stimulate normalization of a condition of the patient's heart; monitoring one or more parameters in response to the delivered remodeling pacing; determining whether the cardiac remodeling pacing has an effect on cardiac normalization in response to the monitoring; and adjusting the cardiac remodeling pacing in response to the determined effect on cardiac normalization.

According to another example of the present disclosure, a cardiac device for delivering a cardiac remodeling pacing to a patient, comprises: a housing; a plurality of electrodes electrically connected to the housing to deliver the cardiac remodeling pacing to stimulate normalization of a condition of the patient's heart; and a processor positioned within the housing and configured to determine one or more parameters in response to the delivered cardiac remodeling pacing, determine whether the cardiac remodeling pacing has an effect on cardiac normalization in response to the monitoring, and adjust the cardiac remodeling pacing in response to the determined effect on cardiac normalization.

In another example of the present disclosure a method, comprises delivering cardiac remodeling pacing to stimulate normalization of a condition of the patient's heart; performing short-term monitoring of one or more parameters in response to the delivered cardiac remodeling pacing; monitoring one or more long-term parameter indicative of a long-term effect of the delivered cardiac remodeling pacing on cardiac normalization; determining the long-term effect of the delivered cardiac remodeling pacing on cardiac normalization in response to the monitoring; and adjusting the cardiac remodeling pacing in response to one or both of the short-term monitoring and the determined long-term effect on cardiac normalization.

In another example of the present disclosure, cardiac device for delivering a cardiac remodeling pacing to a patient, comprises a housing; a plurality of electrodes electrically connected to the housing to deliver cardiac remodeling pacing to stimulate normalization of a condition of the patient's heart; and a processor positioned within the housing and configured to perform short-term monitoring of one or more parameters in response to the delivered cardiac remodeling pacing, monitor one or more long-term parameter indicative of a long-term effect of the delivered cardiac remodeling pacing on cardiac normalization, determine the long-term effect of the delivered cardiac remodeling pacing on cardiac normalization in response to the monitoring, and adjust the cardiac remodeling pacing in response to one or both of the short-term monitoring and the determined long-term effect on cardiac normalization.

DETAILED DESCRIPTION OF EXEMPLARY EMBODIMENTS

It will be apparent to a skilled artisan that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale.

Figure 1:
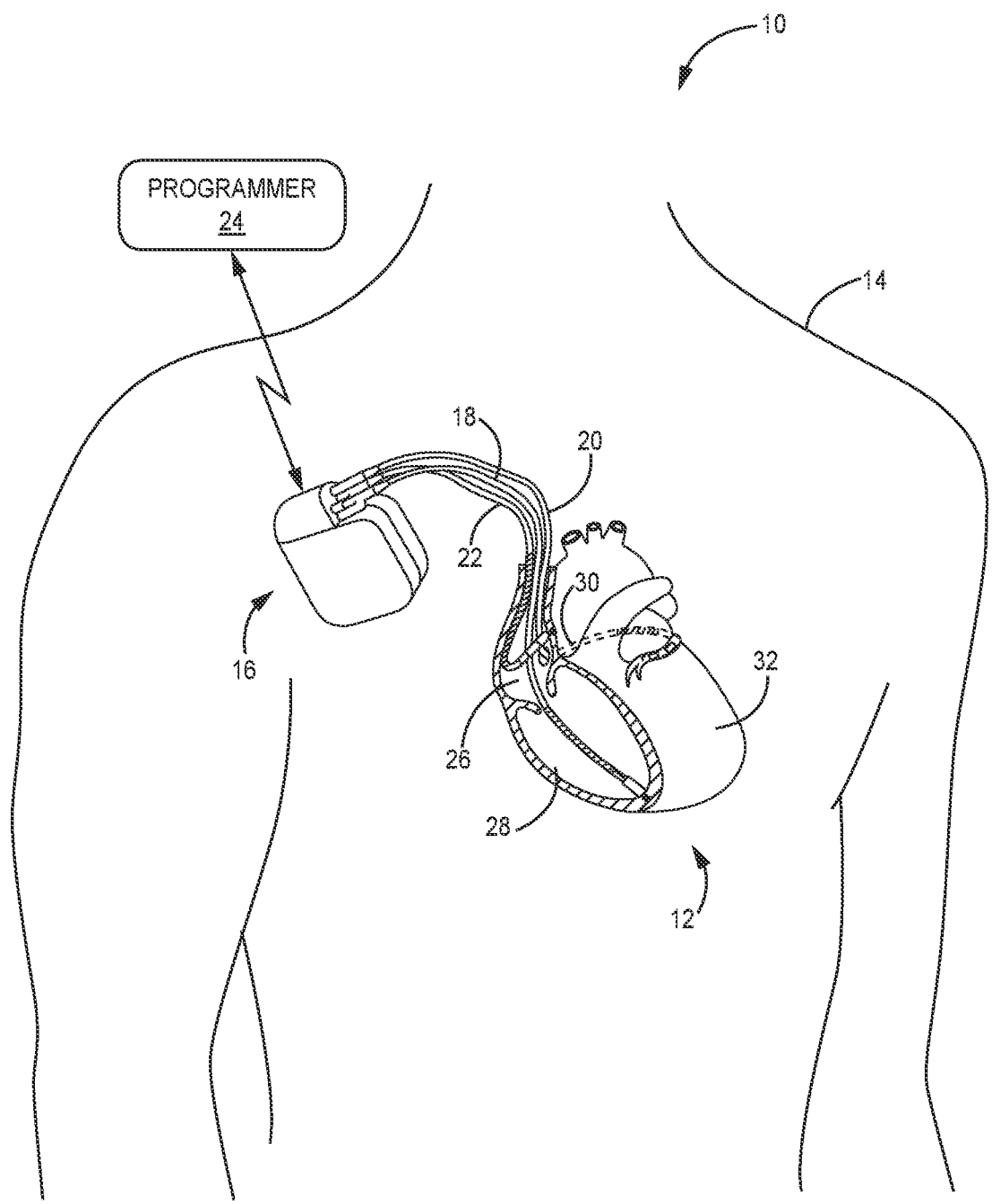
FIG. 1 is a schematic diagram of an exemplary cardiac therapy delivery system that may be used to deliver a pacing therapy according to the present disclosure.

FIG. 1 is a schematic diagram of an exemplary cardiac therapy delivery system that may be used to deliver a pacing therapy according to the present disclosure. The therapy delivery system 10 may include an implantable medical device 16 (IMD), which may be coupled to leads 18, 20, 22 and a programmer 24. The IMD 16 may be, e.g., an implantable pacemaker, cardioverter, and/or defibrillator, that provides electrical signals to the heart 12 of a patient 14 via electrodes coupled to one or more of the leads 18, 20, 22. Patient 14 may, but not necessarily, be a human.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12. In one example, the atrial lead 22 can be positioned near the AV nodal/septal area for delivery of His bundle pacing and at least one of the ventricular lead 18 is positioned in the right ventricle or the ventricular lead 20 is positioned in the left ventricle, as described below.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pulse duration, voltage amplitude, burst length, etc. Further, the IMD 16 may be operable to use various electrode configurations to deliver pacing therapy, which may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning one or more detected or indicated faults associated within the IMD 16 and/or the pacing therapy delivered therewith. The IMD 16 and the programmer 24 may communicate via wireless communication using any techniques known in the art. Examples of communication techniques may include, e.g., low frequency or radiofrequency (RF) telemetry, but other techniques are also contemplated.

Figure 2:
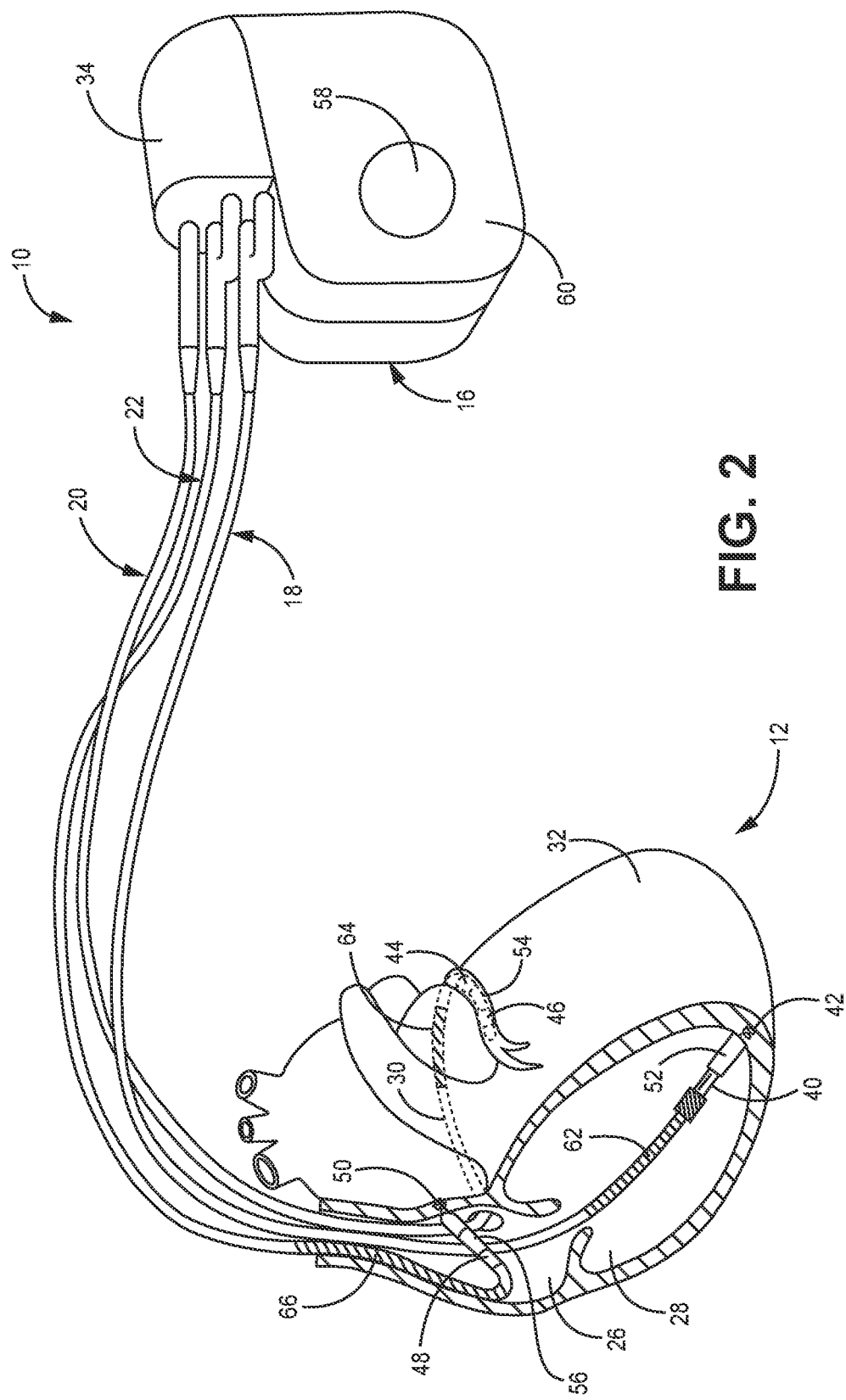
FIG. 2 is a schematic diagram illustrating the exemplary cardiac therapy delivery system of FIG. 1 in more detail.

FIG. 2 is a schematic diagram illustrating the exemplary cardiac therapy delivery system of FIG. 1 in more detail. The leads 18, 20, 22 may be electrically coupled to a therapy delivery module (e.g., for delivery of pacing therapy), a sensing module (e.g., one or more electrodes to sense or monitor electrical activity of the heart 12 for use in determining effectiveness of pacing therapy), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22.

The electrodes 40, 44, 48 may take the form of ring electrodes, and the electrodes 42, 46, 50 may take the form of extendable helix tip electrodes mounted retractably within the insulative electrode heads 52, 54, 56, respectively. Each of the electrodes 40, 42, 44, 46, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22. The electrodes 40, 42, 44, 46, 48, 50 may further be used to sense electrical signals (e.g., morphological waveforms within electrograms (EGM)) attendant to the depolarization and repolarization of the heart 12. The sensed electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 46, 48, 50 may be used for unipolar sensing or pacing in combination with housing electrode 58. In other words, any of electrodes 40, 42, 44, 46, 48, 50, 58 may be used in combination to form a sensing vector, e.g., a sensing vector that may be used to evaluate and/or analysis the effectiveness of pacing therapy. An example of a configuration sensing and pacing may be seen with respect to U.S. Pat. No. 9,002,454 filed Dec. 18, 2012, and assigned to the assignee of the present invention, the disclosure of which is incorporated by reference in its entirety herein as modified by preferably using a LVtip (i.e. electrode 46)-RVcoil (i.e. electrode 62) for the pacing vector and the sensing vector. The LVtip to RVcoil vector may be better for performing impedance measurements. This impedance may be inversely correlated to LV chamber size, and may drop as the LV chamber dilates with remodeling pacing. It is generally understood by those skilled in the art that other electrodes can also be selected as pacing and sensing vectors.

As described in further detail with reference to FIGS. 3 and 4, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity during pacing therapy (e.g., for use in analyzing pacing therapy effectiveness) and may be used in combination with any of electrodes 40, 42, 44, 46, 48, 50, 58. In at least one embodiment, the RV elongated electrode 62 may be used to sense electrical activity of a patient's heart during the delivery of pacing therapy (e.g., in combination with the housing electrode 58 forming a RV elongated, coil, or defibrillation electrode-to-housing electrode vector).

The configuration of the exemplary therapy delivery system 10 illustrated in FIGS. 1-2 is merely one example. In one example, the atrial lead 22 is positioned near the AV nodal/septal area for delivery of His bundle pacing and either the ventricle lead 18 is positioned in the right ventricle or the ventricle lead 20 positioned in the left ventricle, or both ventricle leads 18 and 20 may be included, as described below. In addition, the electrode 50 of lead 22 may take the form of a helical tip electrode to enable the lead to be fixedly engaged near the AV nodal/septal area for delivery of His bindle pacing, described below.

Figure 3:
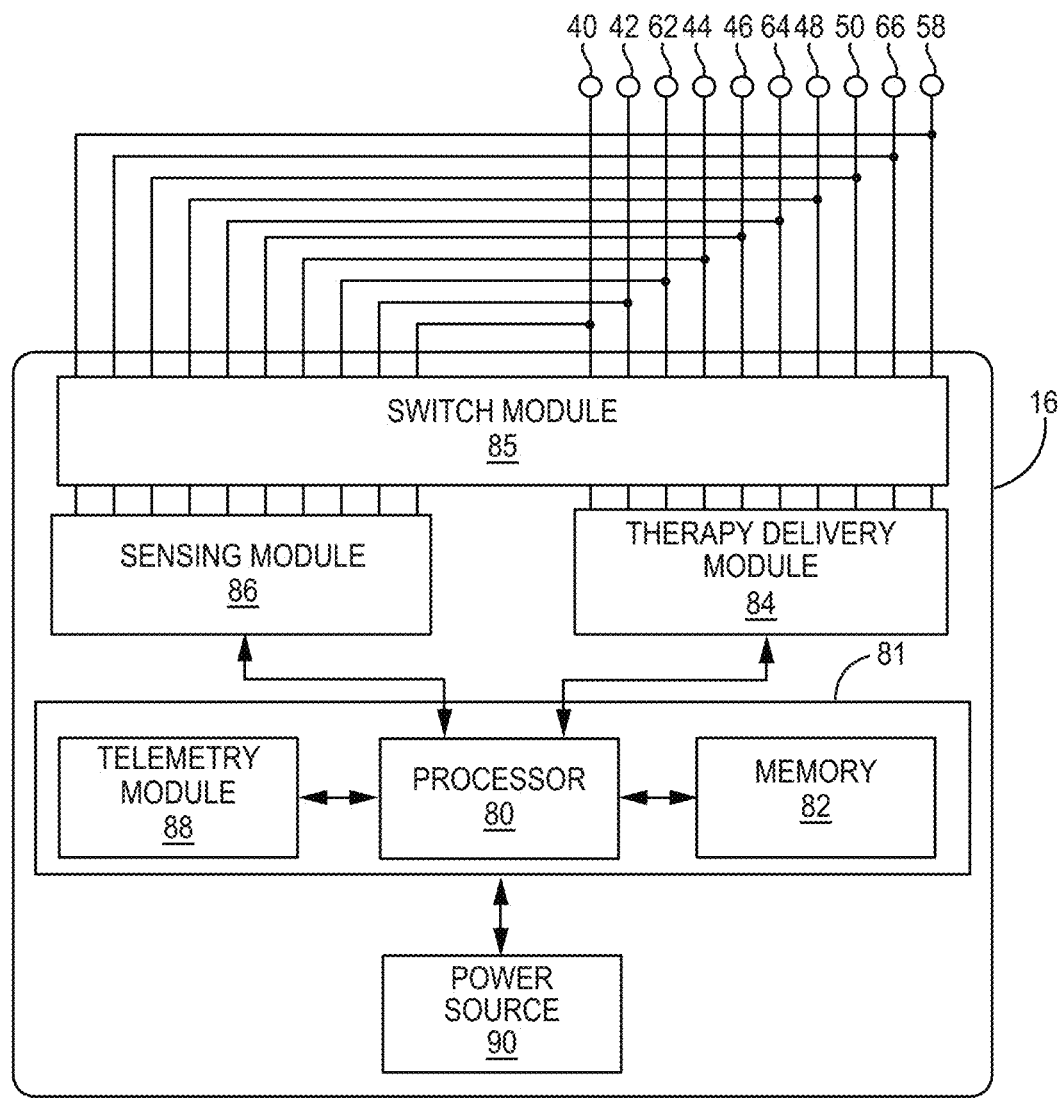
FIG. 3 is an exemplary functional block diagram of an exemplary configuration of an implantable medical device according to an example of the present disclosure.

FIG. 3 is a functional block diagram of an exemplary configuration of an implantable medical device according to an example of the present disclosure. As illustrated in FIG. 3, the IMD 16 may include a control module 81, a therapy delivery module 84 (e.g., which may include a stimulation generator), a sensing module 86, and a power source 90. The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media. Memory 82 includes computer instructions related to capture management, including the method of capture management according to the present disclosure, described in detail below. Furthermore, memory 82 includes computer instructions for one or more pacing regimen(s) (e.g. one or more pacing algorithm(s) etc.). For example, one or more pacing algorithms pace the heart at an elevated heart rate for a specified duration followed by pacing the heart at a second heart rate level for another pre-specified duration of time. One or more other embodiments involve pacing the patient's heart at a first elevated rate and a first duration. In one or more pacing regimens, the pacemaker delivers a first elevated pacing rate (e.g. up to 30 heart beats per minute above resting heart rate for up to 10 minutes or up to 20 minutes). Thereafter, the pacing rate is elevated to a second elevated pacing rate (e.g. up to 20 HBM above the first elevated heart rate for up to 10 or 20 minutes). Thereafter a third pacing rate is delivered to allow the heart to beat more slowly than the second elevated pacing rate. A fourth pacing rate, lower than the third pacing rate, is delivered to the heart through a pacemaker. Thereafter, the heart rate is allowed to gradually return to a resting heart rate level (with or without pacing). Multiple other pacing regimens are disclosed herein that may be employed by a pacemaker in order to remodel the heart.

The processor 80 (also referred to as processor circuit) of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control the therapy delivery module 84 to deliver electrical stimulus such as, e.g., pacing pulses with the amplitudes, pulse widths, frequency, or electrode polarities specified by the selected one or more therapy programs (e.g., pacing therapy programs, pacing recovery programs, capture management programs, etc.). As shown, the therapy delivery module 84 is electrically coupled to electrodes 40, 42, 44, 46, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 46, 48, 50, 58, 62, 64, 66.

For example, therapy delivery module 84 may deliver pacing stimulus (e.g., pacing pulses) via ring electrodes 40, 44, 48 coupled to leads 18, 20, and 22, respectively, and/or helical tip electrodes 42, 46, and 50 of leads 18, 20, and 22, respectively. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured to deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 46, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 46, 48, 50, 58, 62, 64, 66 to monitor electrical activity of the heart 12, e.g., electrocardiogram (ECG)/electrogram (EGM) signals, etc. The ECG/EGM signals may be used to analyze a plurality of paced events. More specifically, one or more morphological features of each paced event within the ECG/EGM signals may be used to determine whether each paced event has a predetermined level of effectiveness. The ECG/EGM signals may be further used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used to, e.g., sense electrical activity of the patient's heart (e.g., one or more electrical vectors of the patient's heart using any combination of the electrodes 40, 42, 44, 46, 48, 50, 58, 62, 64, 66). In some examples, the control module 81 may select the electrodes that function as sensing electrodes via the switch module within the sensing module 86, e.g., by providing signals via a data/address bus. In some examples, the sensing module 86 may include one or more sensing channels, each of which may include an amplifier.

In some examples, sensing module 86 includes a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an EGM. In some examples, the storage of such EGMs in memory 82 may be under the control of a direct memory access circuit. The control module 81 (e.g., using the processor 80) may employ digital signal analysis techniques to characterize the digitized signals stored in memory 82 to analyze and/or classify one or more morphological waveforms of the EGM signals to determine pacing therapy effectiveness. For example, the processor 80 may be configured to determine, or obtain, one or more features of one or more sensed morphological waveforms within one or more electrical vectors of the patient's heart and store the one or more features within the memory 82 for use in determining effectiveness of pacing therapy at a later time.

If IMD 16 is configured to generate and deliver pacing pulses to the heart 12, the control module 81 may include a pacer timing and control module, which may be embodied as hardware, firmware, software, or any combination thereof. The pacer timing and control module may include one or more dedicated hardware circuits, such as an ASIC, separate from the processor 80, such as a microprocessor, and/or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), "A" may indicate an atrium, and "R" may indicate rate responsive. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within control module 81 may include atrial and ventricular pacing escape intervals, refractory periods during which sensed P-waves and R-waves are ineffective to restart timing of the escape intervals, and/or the pulse widths of the pacing pulses. As another example, the pacer timing and control module may define a blanking period and provide signals from sensing module 86 to blank one or more channels, e.g., amplifiers, for a period during and after delivery of electrical stimulation to the heart 12. The durations of these intervals may be determined in response to stored data in memory 82. The pacer timing and control module of the control module 81 may also determine the amplitude of the cardiac pacing pulses.

During pacing, escape interval counters within the pacer timing/control module may be reset upon sensing of R-waves and P-waves. Therapy delivery module 84 (e.g., including a stimulation generator) may include one or more pacing output circuits that are coupled, e.g., selectively by the switch module 85, to any combination of electrodes 40, 42, 44, 46, 48, 50, 58, 62, or 66 appropriate for delivery of a bipolar or unipolar pacing pulse to one of the chambers of heart 12. The control module 81 may reset the escape interval counters upon the generation of pacing pulses by therapy delivery module 84, and thereby control the basic timing of cardiac pacing functions, including anti-tachyarrhythmia pacing.

In some examples, the control module 81 may operate as an interrupt driven device and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer. In at least one embodiment, the telemetry module 88 may be configured to transmit an alarm, or alert, if the pacing therapy becomes ineffective or less effective (e.g., does not have a predetermined level of effectiveness).

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 4:
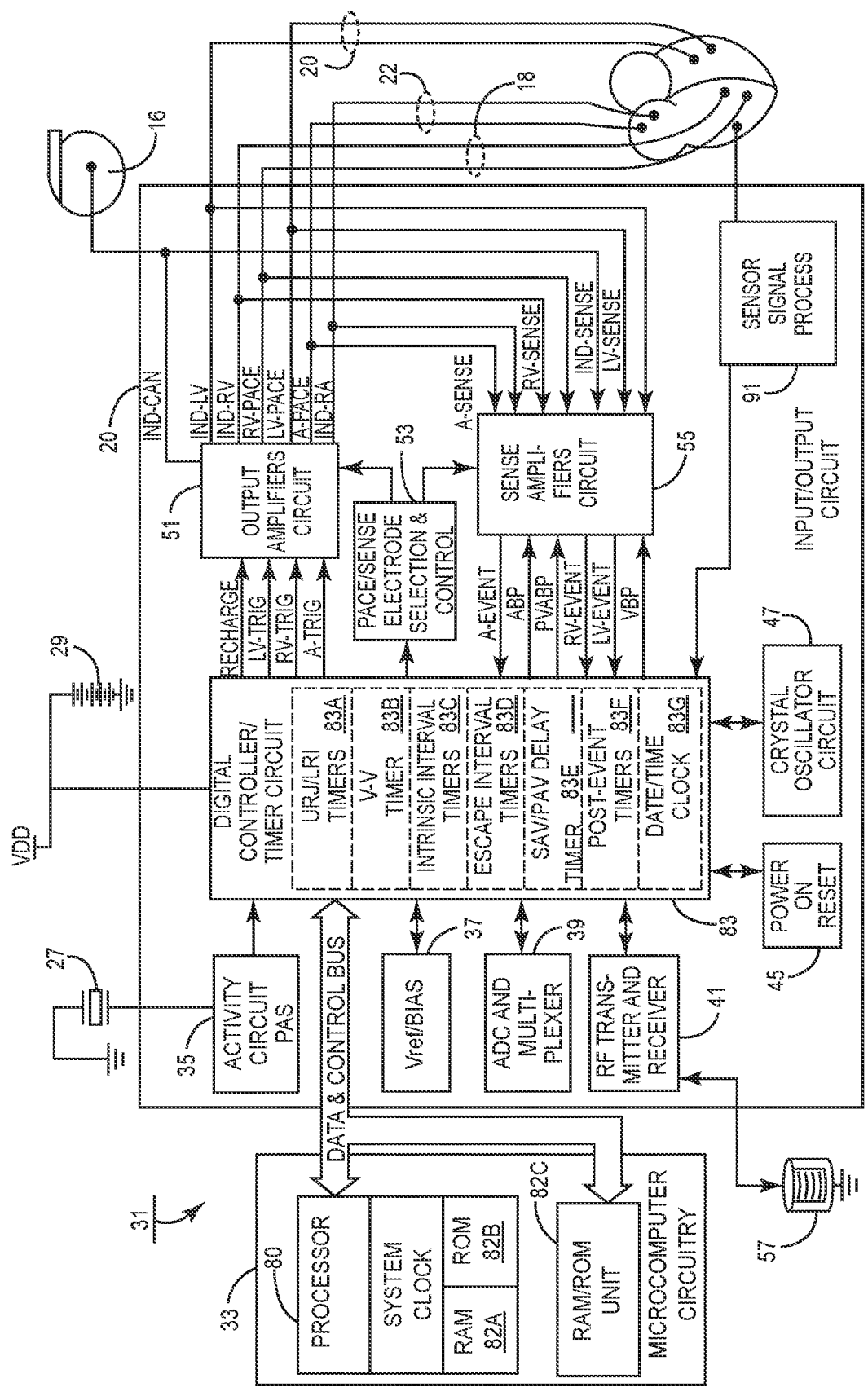
FIG. 4 is an exemplary functional block diagram of circuitry of an implantable medical device according to the present disclosure.

FIG. 4 is an exemplary functional block diagram of circuitry of an implantable medical device according to the present disclosure. FIG. 4 depicts bipolar RA lead 22, bipolar RV lead 18, and bipolar LV CS lead 20 without the LA CS pace/sense electrodes leading into the right ventricle 28 (FIG. 1) and into the coronary sinus 30 (FIG. 1) coupled with an implantable pulse generator (IPG) circuit 31 having programmable modes and parameters of a bi-ventricular DDD/R type known in the pacing art. In turn, the sensor signal processing circuit 91 indirectly couples to the digital controller/timer circuit 83 and via data and control bus to microcomputer circuitry 33. The IPG circuit 31 is illustrated in a functional block diagram divided generally into a microcomputer circuitry 33 and a pacing circuit. The pacing circuit includes the digital controller/timer circuit 83, the output amplifiers circuit 51, the sense amplifiers circuit 55, the RF telemetry transceiver transmitter and receiver 41, the activity sensor circuit 35 as well as a number of other circuits and components described below.

Crystal oscillator circuit 47 provides the basic timing clock for the pacing circuit while battery 29 provides power. Power-on-reset circuit 45 responds to initial connection of the circuit to the battery for defining an initial operating condition and similarly, resets the operative state of the device in response to detection of a low battery condition. Voltage reference and bias circuit 37 generates stable voltage reference and currents for the analog circuits within the pacing circuit, while analog to digital converter (ADC) and multiplexer 39 digitizes analog signals and voltage to provide real time telemetry of cardiac signals from sense amplifiers 55, for uplink transmission via RF transmitter and receiver 41. Voltage reference and bias circuit 37, ADC and multiplexer 39, power-on-reset circuit 45 and crystal oscillator circuit 47 may correspond to any of those presently used in current marketed implantable cardiac pacemakers.

The IPG generates pacing pulses to cardiac tissue. Typically, pacing pulses can be timed to a target heart rate for each patient. To adjust a patient's heart rate, the interval between pacing pulses is adjusted by the pacemaker. For example, to increase a patient's heart rate, the interval between pulses generated from the pacemaker is decreased. In contrast, to decrease a patient's heart rate, the interval between pulses is increased. In one or more embodiments, an exercise regimen may be configured to include exercise intervals (i.e. higher target heart rate that is higher than a patient's resting heart rate level) interleaved with recovery intervals (i.e. lower target heart rate that are lower than an immediately preceding exercise interval). One target heart rate zone for exercising the heart may be 50-85% of a patient's maximum heart rate. In one or more embodiments, the target heart rate zone can be set to 75-95% of the patient's maximum heart rate zone. In one or more other embodiments, the target heart rate zone can be set up to 105% of the patient's maximum heart rate zone for a short period of time (e.g. up to 20 minutes, or up to 30 minutes etc.)

The exercise regimens, comprising a set of increased rate intervals interleaved with recovery rate intervals (also referred to as reduced rate intervals), can be implemented by using a base rate that is adjusted by modifying the pacing pulses for each interval. For example, if the resting heart rate is the base rate from which the intervals are measured, then the first increased rate can be determined by taking the average resting heart rate for that patient (e.g. 60 HBM) adding a pre-specified number of HBMs (e.g. 20 HBMs etc.) for that particular interval to obtain 80 HBM (i.e. 60 HBM+20 HBM) over a first time period (e.g. 10 minutes). Since the target heart rate level is now 80 HBM, the interval between pulses generated from the pacemaker is decreased.

The pacemaker can be configured to use the maximum heart rate level as a base rate and a target rate would be adjusted down from the maximum heart rate to a target heart rate zone (e.g. 50%-85% of the maximum heart rate zone). The patient's maximum heart rate can be determined by using the patient's tracked daily activities or using known equations (i.e. 220 HBPM minus the patient's age). Maximum heart rate can depend on a variety of factors including the patient's age, physical activity, and heart condition.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 35 in the depicted, exemplary IPG circuit 31. The patient activity sensor 35 is coupled to the IPG housing and may take the form of a piezoelectric crystal transducer as is well known in the art and its output signal is processed and used as the RCP. Sensor 27 generates electrical signals in response to sensed physical activity that are processed by activity circuit 35 and provided to digital controller/timer circuit 83. Activity circuit 35 and associated sensor 27 may correspond to the circuitry disclosed in U.S. Pat. Nos. 5,052,388 and 4,428,378.

Conventional pacemakers are presently configured to automatically track a person's heart rate for a certain period of time (e.g. 1 day) and customize the pacing pulse intervals in response to the patient's activity. The activity sensor senses the person's activities throughout the day and the processor adjusts the pacing rate of the pacemaker to the patient's activities. After a person's heart rate has been tracked for a day, a rate profile optimization is automatically performed, as fully described in Medtronic Manual CLARIA MRI™/CLARIA MRI™ QUAD CRT-Ds reference manual M963432A001, incorporated by reference in its entirety and freely available from Medtronic, Inc. located at 710 Medtronic Parkway, Minneapolis, Minn. 55432. The goal of the rate profile optimization is to ensure that the rate response of the pacemaker remains appropriate for the full range of patient activities. Each day, the pacemaker collects and stores daily and long-term averages of the percentage of time that the patient sensor-indicated rate is at different pacing rates. The pacemaker then uses the ADL Response and exertion response parameters to define the percentage of time that the pacing rate stays in the ADL rate range and exertion rate range, respectively. Based on daily comparisons, the pacemaker automatically adjusts the ADL Setpoint, the UR Setpoint, or both setpoints. During implementation of the exercise regimen, the rate profile optimization recognizes that the heart is being intentionally exercised and does not reduce the pacing.

Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer circuitry 33 contains a processor 80 and associated system clock and on-processor RAM and ROM chips 82A and 82B, respectively. In addition, microcomputer circuitry 33 includes a separate RAM/ROM chip 82C to provide additional memory capacity. Processor 80 normally operates in a reduced power consumption mode and is interrupt driven. Processor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuitry 33 by means of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the processor 80 may also serve to define variable, operative AV delay intervals and the energy delivered to each ventricle.

In one embodiment, processor 80 is a custom microprocessor adapted to fetch and execute instructions stored in RAM/ROM unit 82C in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of processor 80.

Digital controller/timer circuit 83 operates under the general control of the microcomputer circuitry 33 to control timing and other functions within the pacing circuit and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post event timer 83F for timing post-ventricular time periods, and a date/time clock 83G.

The AV delay interval timer 83E is loaded with an appropriate delay interval for one ventricular chamber (i.e., either an A-RVp delay or an A-LVp delay as determined using known methods) to time-out starting from a preceding A-PACE or A-EVENT. The AV delay interval timer 83E triggers pacing stimulus delivery, and can be based on one or more prior cardiac cycles (or from a data set empirically derived for a given patient).

The post-event timers 83F time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer circuitry 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The processor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the indifference can (IND_CAN) electrode 20 to the RA pace pulse generator (and LA pace pulse generator if provided), RV pace pulse generator and LV pace pulse generator. Pace/sense electrode selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. It has been common in the prior art to use very high impedance P-wave and R-wave sense amplifiers to amplify the voltage difference signal which is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the sense amplifiers circuit 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND_CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND_CAN electrode 20 to the RA sense amplifier (and LA sense amplifier if provided), RV sense amplifier and LV sense amplifier. Again, pace/sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory and can inadvertently be triggered by electrical noise signals or aberrantly conducted depolarization waves rather than true R-waves or P-waves.

Figure 5:
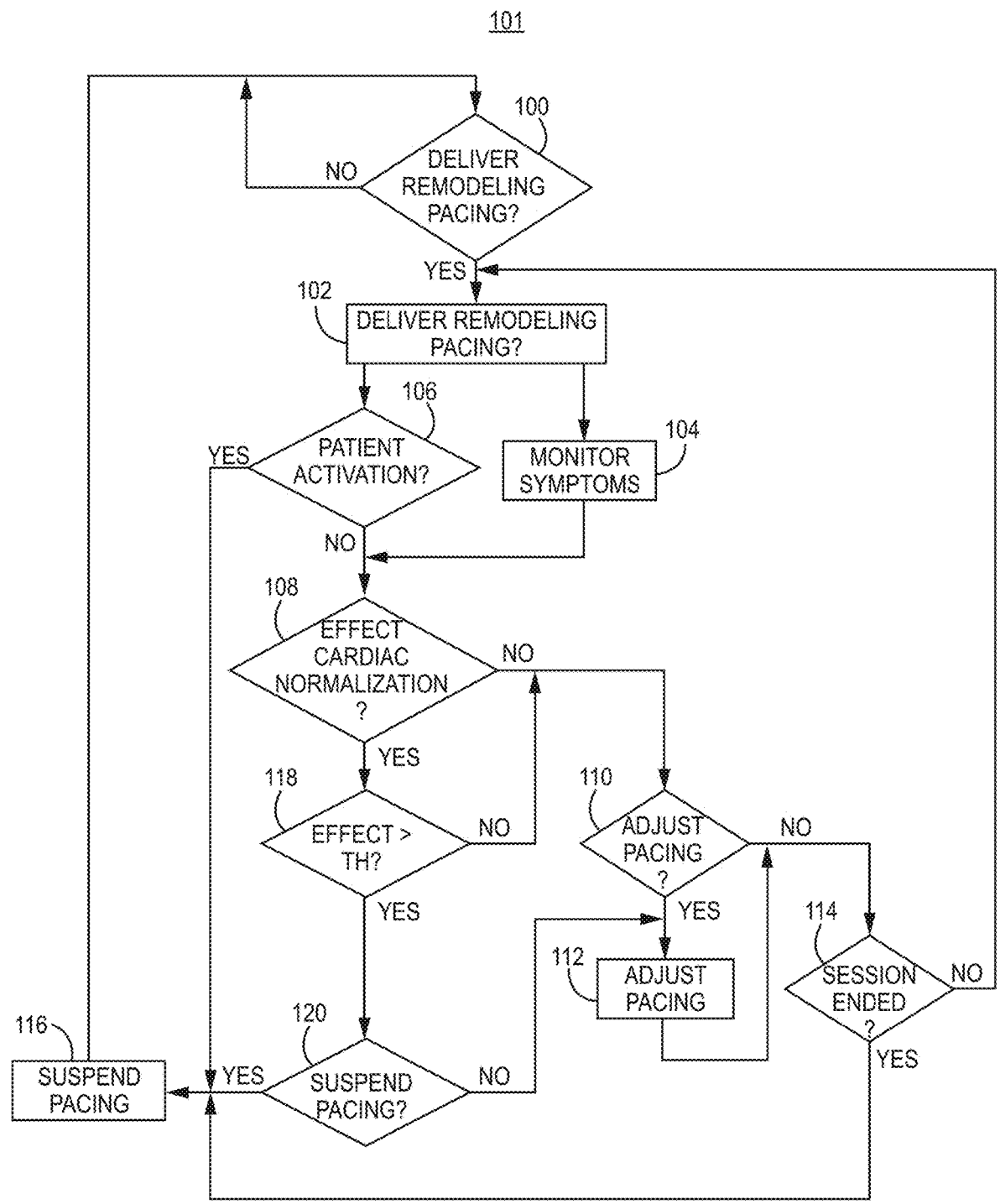
FIG. 5 is a flowchart of a method of delivering a pacing therapy for cardiac remodeling according to an example of the present disclosure.

FIG. 5 is a flowchart of a method of using a pacemaker to deliver a pacing therapy capable of remodeling the heart over a period of time according to an example of the present disclosure. In one or more embodiments, the pacing therapy may result in cardiac remodeling. According to one example, pacing therapy for cardiac remodeling may be delivered using the atrial lead 22 positioned near the AV nodal/high septal area for delivery of pacing via the tip electrode 50 and ring electrode 48. Skilled artisans appreciate that other pacing vectors may be used to pace the heart (e.g. His bundle therapy as described in US Patent Application No. 62/581,486 filed on Nov. 3, 2018 and U.S. Patent Application No. 62/573,685 filed on Oct. 17, 2018, incorporated by reference in their entirety. According to one example of the present disclosure, remodeling pacing therapy may be delivered at a predetermined time of the day. For example, pacing therapy can be delivered when the patient is most likely to be inactive (e.g. patient is asleep or in a supine position). Inactivity can be determined in a variety of ways (e.g. detection monitoring, historical data gathered from wearable devices having sensors (e.g. watch such as Garmin™ etc.), or user-inputted information. A patient can be determined to be inactive when a resting heart rate is detected, such as when the patient is asleep or in a supine position. Alternatively, the pacing therapy can be automatically delivered manually or without sensing any data (e.g. at a certain time of day (e.g. night time)). Therefore, as illustrated in FIG. 5, in a method of delivering a pacing therapy via a pacemaker device for cardiac remodeling 101 according to an example of the present disclosure, the processor 80 may determine whether to initiate delivery of remodeling pacing therapy, Block 100. For example, processor 80 may determine that it is a predetermined time of day when the patient is most likely to inactive, such as between the hours of 12 A.M.-5 P.M., for example, or by determining that activity of the patient sensed via an activity sensor is less than a predetermined threshold indicative of the patient being asleep and/or in a supine position.

Upon determining that delivery of the remodeling pacing is scheduled, Yes in Block 100, the processor 80 may deliver the remodeling pacing therapy, Block 102, at a predetermined rate and/or duration. For example, the processor 80 may cause the remodeling pacing to be delivered at an elevated rate (e.g., 100 bpm for a 30-minute duration), or in another example at an elevated rate (e.g., 100 bpm, etc., for a certain period of time, e.g., 5 hours per day). In another example, the processor 80 may cause the remodeling pacing to be delivered at an initial lower rate, such as 70 bpm, and gradually increase the patient's heart rate to a predetermined heart rate threshold, such as 100 bpm, for example. Exemplary patterns for delivering the remodeling pacing at variable rates and/or durations are described in detail below. Additionally, exercising the heart may continue for a period of time, with an adjusted pacing parameter (e.g. amplitude etc.) to increase heart rate, and/or until detection of a termination condition.

Once delivery of the remodeling pacing is initiated, Block 102, the processor 80 may begin monitoring symptoms of the patient resulting from the delivered remodeling pacing, Block 104. In addition, the processor 80 may monitor whether a patient activation signal has been received from the patient. Examples of the patient activation signal may be either a signal initiated by the patient indicating that the patient is experiencing discomfort as a result of the delivered remodeling pacing, or a signal received from the activity sensor 35 indicating the patient is no longer asleep or in a supine position, Block 106. If the processor 80 determines that a patient activation signal has been received, Yes in Block 106, the processor 80 suspends delivery of the remodeling pacing therapy, Block 116, and waits for the next scheduled session for delivery of remodeling pacing, Block 100.

Based on the monitored symptoms, Block 104, and if a patient activation signal has not been received, No in Block 106, the processor 80 determines whether the delivered remodeling pacing results in there being a measurable effect that would indicate that the delivery of the remodeling pacing is effective in causing some level of normalization of the condition of patient's heart, Block 108. For example, the processor 80 may monitor changes in one or more parameters, such as tissue perfusion, atrial perfusion, estimated pulmonary artery diastolic pressure (ePad), right ventricular pressure, left ventricular pressure, and a pressure surrogate, such as impedance, as indicators that the remodeling pacing is affecting the overall condition of the patient's heart in a way that is indicative of there being some level of cardiac normalization. In one or more other embodiments, therapy is automatically delivered and/or suspended after a period of time (e.g. suspend therapy after 30 minutes after delivering pacing, 1 hour etc.) without detection of a parameter such as tissue perfusion, atrial perfusion, estimated pulmonary artery pressure (ePad), right ventricular pressure, left ventricular pressure, and a pressure surrogate, such as impedance.

In one example, in order to determine whether there is a measurable normalization effect, Block 108, the processor 80 may determine whether there is a change in perfusion associated with the patient. For example, change in tissue perfusion may be determined by measuring tissue perfusion during delivery of the remodeling pacing therapy and comparing the measured tissue perfusion with a non-paced baseline tissue perfusion level determined prior to the remodeling pacing being delivered to the patient, such as at implant of the device, for example. While the description below uses tissue perfusion as a target parameter to adjust therapy, other parameters mentioned above can be used as well.

If the current measured level of tissue perfusion has not increased relative to the baseline tissue perfusion level, the processor 80 determines that the delivered remodeling pacing has not resulted in there being a measurable effect indicative of cardiac normalization, No in Block 108. A determination is then made as to whether to adjust delivery of the remodeling pacing, Block 110, in order to increase the likelihood that subsequently delivered remodeling pacing will result in a measurable effect indicative of cardiac normalization.

Figure 6:
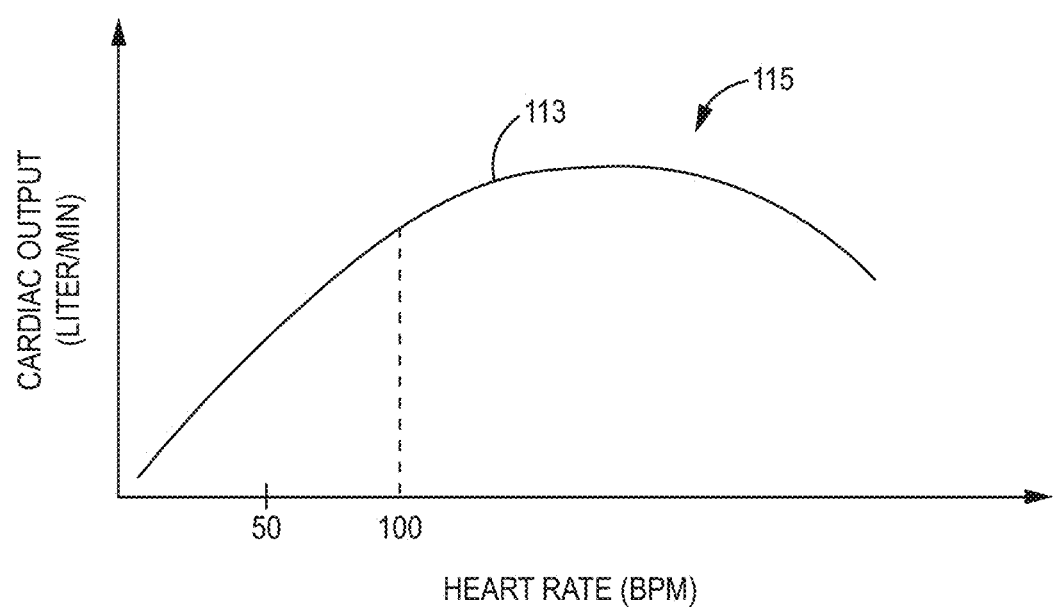
FIG. 6 is a graphical representation illustrating the effect of remodeling pacing on cardiac output of a patient.

FIG. 6 is a graphical representation illustrating the effect of remodeling pacing on cardiac output of a patient. Cardiac output (CO) refers to the amount of blood pumped by the heart per minute, and is the product of the heart rate (HR) or number of beats per minute and the stroke volume (SV), which is the amount of blood pumped per beat, so that CO=HR×SV. As illustrated in FIG. 6, cardiac output typically increases as the heart rate increases until a maximum increase in cardiac output 113 is achieved. This maximum output 113 tends to vary from patient to patient and may vary for a single patient, depending upon a current condition of the patient's heart. Once the maximum cardiac output 113 is achieved, any further increase in the paced heart rate results in a reduction of the patient's cardiac output 115 and may likely indicate detrimental effects to the patient's cardiac condition.

Therefore, in order to determine whether to adjust the pacing therapy, Block 110 of FIG. 5, when a measurable effect indicative of cardiac normalization is not being detected, No in Block 108, the processor 80 may determine to adjust the pacing therapy, Yes in Block 110, if a slope of the cardiac output of the patient is determined to be increasing. The processor 80 may then adjust the remodeling pacing by increasing the rate and/or the duration of the remodeling pacing, Block 112. The typical intervention adjustments favor increasing the maximum pacing rate, with increasing duration as a secondary adjustment should rate effects become symptomatic. However, if the slope of the cardiac output of the patient is not determined to be increasing, the processor 80 determines not to adjust the pacing therapy, No in Block 110.

Once the processor 80 either determines to adjust the therapy, Yes in Block 110, and therefore the remodeling pacing is adjusted, Block 112, or the processor 80 determines not to adjust the therapy, No in Block 110, a determination is made as to whether the session time has ended, Block 114. For example, the processor 80 may determine whether the remodeling pacing therapy has been delivered at a rate of least 100 bpm for a certain period of time (e.g., 30 minutes, etc.), or in another example whether the remodeling pacing therapy has been delivered at a rate of at least 100 bpm for 5 hours per day.

If the session time has not ended, No in Block 114, the processor 80 continues delivering the remodeling pacing therapy, Block 102, using either the same or the adjusted rate and/or duration. On the other hand, if the session time has ended, Yes in Block 114, the processor 80 suspends delivery of the remodeling pacing therapy, Block 116, and waits for the next scheduled session for delivery of remodeling pacing, Block 100.

If the current measured level of tissue perfusion has increased relative to the baseline tissue perfusion level, the processor 80 determines that the delivered remodeling pacing has resulted in there being a measurable effect indicative of cardiac normalization, Yes in Block 108. A determination is then made as to whether the effect is greater than a predetermined symptom avoidance threshold, Block 118, indicative of the remodeling pacing being too aggressive for the patient. If the effect is determined to be greater than the predetermined symptom avoidance threshold, Yes in Block 118, the processor 80 determines whether to adjust and continue delivery of the adjusted remodeling pacing therapy or to suspend delivery of the remodeling therapy to address the indication of the remodeling pacing being too aggressive for the patient, Block 120.

For example, the processor 80 may determine the effect to be greater than the predetermined symptom avoidance threshold, Yes in Block 118, and therefore that the remodeling therapy is too aggressive, if there has been an increase in the number of premature ventricular contractions (PVCs) that have occurred during delivery of the remodeling pacing. When increased PVCs is the indication used in Block 118 to determine that the remodeling pacing is too aggressive, the processor 80 determines not to suspend delivery of the remodeling pacing, No in Block 120, and therefore adjusts the pacing therapy in Block 112, Yes in Block 120, by reducing the rate of delivery of pacing by a predetermined increment. For example, the delivery rate may be reduced by 10 beats per minute. In another example, the processor 80 may track an original baseline slope and suspend therapy when the slope deviates from the baseline slope by a predetermined amount or percentage.

In another example, the processor 80 may determine the effect to be greater than the predetermined symptom avoidance threshold, Yes in Block 118, and therefore that the remodeling therapy is too aggressive, if a measure of contractility threshold is determined to be satisfied. For example, determining whether a measure of contractility is satisfied may include determining whether there is a decrease in amplitudes of S1 and S2 heart sounds sensed via a heart sounds sensor, or whether an S3 heart sound is sensed via the heart sensor during the delivered remodeling pacing. Many pacemakers are configured to detect heart sounds. Exemplary pacemakers AMPLIA™ or CLARIA™, available from Medtronic, Inc. located in Minneapolis, Minn., are configured to detect heart sounds. When a measure of contractility threshold is the indication used in Block 118 to determine that the remodeling therapy is too aggressive, the processor 80 determines to suspend delivery of the remodeling pacing, Yes in Block 120, as a result of the indication, and therefore suspends delivery of the remodeling pacing therapy, Block 116, and waits for the next scheduled session for delivery of remodeling pacing, Block 100.

In yet another example, the processor 80 may determine the effect to be greater than the predetermined symptom avoidance threshold, Yes in Block 118, and therefore that the remodeling therapy is too aggressive, if a biomarker indicator exceeds a biomarker indicator threshold. For example, determining whether a biomarker indicator exceeds a biomarker indicator threshold may include determining whether a biomarker indicator for diagnosing congestive heart failure (CHF), such as brain natriuretic peptide (BNP), also referred to as B-type natriuretic peptide increases beyond a predetermined threshold indicative of CHF. When a biomarker indicator is the indication that was used to determine that the remodeling therapy is too aggressive, the processor 80 determines to suspend delivery of remodeling pacing, Yes in Block 120, as a result of the indication, and therefore suspends delivery of the remodeling pacing therapy, Block 116, and waits for the next scheduled session for delivery of remodeling pacing, Block 100.

In another example, the processor 80 may determine the effect to be greater than the predetermined symptom avoidance threshold, Yes in Block 118, and therefore that the remodeling therapy is too aggressive, if ST segment measurements are determined to satisfy an ST segment threshold. For example, ST segment measurements may be determined during the delivered remodeling pacing based on ECG signals sensed by the IMD 16 or based on EGM cardiac signals sensed by another internal or external monitoring device sensed from an alternate location. In one or more embodiments, data is stored (such as in a table) into memory for a patient in which the data associates ST segments with an acceptable pacing therapy result so pacing can continue and/or the ST segment is associated with a too aggressive pacing therapy in order to suspend therapy. The ST segment measurements determined during the delivered pacing are compare to an ST threshold, which may be determined during non-paced cardiac activity, and if an increase in the ST segment measurements is determined to occur, the ST segment threshold is determined to be satisfied. When changes in ST segment measurements is the indication used in Block 118 to determine that the remodeling therapy is too aggressive, the processor 80 determines not to suspend delivery of the remodeling pacing, No in Block 120, and therefore adjusts the pacing therapy, Yes in Block 120, by reducing the rate of delivery of pacing by a predetermined increment.

Once the processor 80 adjusts delivery of the remodeling pacing, Block 112, either to address instances of the remodeling pacing therapy being too aggressive, Yes in Block 118, or to address instances of the remodeling pacing therapy not resulting in there being a measurable normalization effect, No in Block 108, a determination is then made as to whether the session time has ended, Block 114. For example, the processor 80 may determine whether the remodeling pacing therapy has been delivered at a rate of at least 100 bpm for 30 minutes. In another example, the processor 80 may determine whether the remodeling pacing therapy has been delivered at a rate of at least 100 bpm for 5 hours per day for a two-week period of time. If the session time has not ended, No in Block 114, the processor 80 continues delivering the remodeling pacing therapy, Block 102, and the therapy continues. On the other hand, if the session time has ended, Yes in Block 114, the processor 80 suspends delivery of the remodeling pacing therapy, Block 116, and waits for the next scheduled delivered remodeling pacing session, Block 100.

In this way, a method for delivering a cardiac remodeling pacing therapy according to an example of the present disclosure may include the processor 80 sensing a cardiac signal via the tip electrode 50 and the ring electrode 48 of the atrial lead 22 and monitoring cardiac symptoms to determine whether undesirable symptoms are induced as a result of the delivered remodeling pacing. For example, the processor 80 may deliver cardiac remodeling pacing to stimulate normalization of a condition of the patient's heart, monitor one or more parameters in response to the delivered remodeling pacing, determine an effect on cardiac normalization in response to the monitoring, and adjust the remodeling pacing in response to the determined effect on cardiac normalization.

Figure 7:
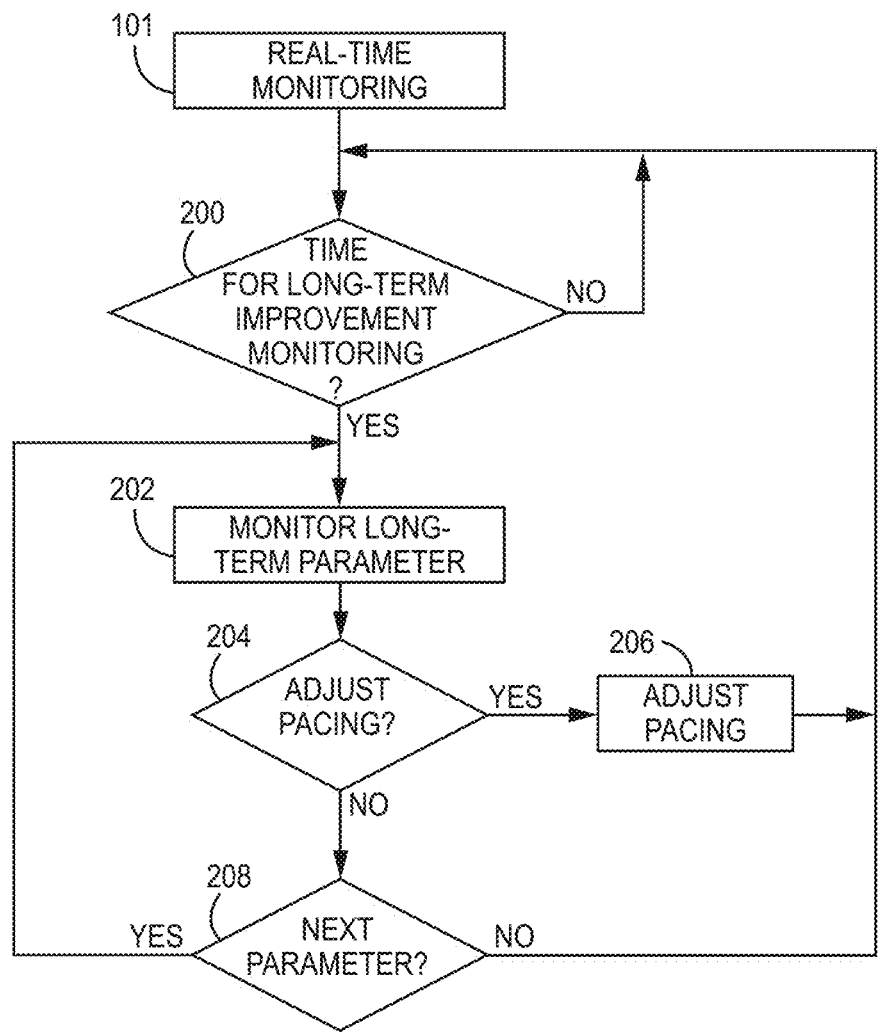
FIG. 7 is a flowchart of a method of delivering a pacing therapy for cardiac remodeling according to an example of the present disclosure.

FIG. 7 is a flowchart of a method of delivering a pacing therapy for cardiac remodeling according to an example of the present disclosure. According to another example, during real-time delivery of the remodeling pacing therapy, the processor 80 may determine whether undesirable symptoms are induced as a result of the delivered remodeling pacing based on short-term symptom avoidance factors, and adjust or suspend the delivered therapy accordingly, as described above. In addition, the processor 80 may also monitor long-term efficacy improvement factors to determine whether there is long-term improvement in the cardiac condition as a result of the delivered remodeling pacing therapy over an extended period of time. In particular, once the remodeling pacing therapy has been delivered for a predetermined long-term period of time, such as being delivered at a rate of at least 100 bpm for 5 hours per day for a two-week period of time, for example, the processor 80 may begin performing long-term monitoring of the effects of the remodeling pacing to determine whether there has been a desired level of improvement towards cardiac normalization.

For example, as illustrated in the example of FIG. 7, during the continuous real-time monitoring of the delivered remodeling pacing 101, described above, the processor 80 evaluates long-term effects of the delivered remodeling pacing to determine whether the remodeling pacing has resulted in there being successful normalization of the patient's heart. For example, once the processor 80 determines that it is time to perform long-term monitoring of the remodeling pacing, Yes in Block 200, i.e., when it is determined that the remodeling pacing has been delivered at a rate of at least 100 bpm for 5 hours per day for a two-week period of time, for example, the processor 80 begins monitoring one or more long-term parameters associated with long-term delivery of the remodeling pacing, Block 202, and evaluates long-term effects of the delivered remodeling pacing to determine whether the remodeling pacing has resulted in there being successful normalization of the patient's heart. A determination is then made, based on the long-term parameter, as to whether to adjust the remodeling pacing, Block 204. If the processor 80 determines that the long-term parameter indicates that the remodeling pacing should be adjusted, Yes in Block 204, the processor 80 adjusts the remodeling pacing, Block 206, and waits for the next scheduled time to perform long-term monitoring of the remodeling pacing, Yes in Block 200. On the other hand, if the processor 80 determines that the long-term parameter indicates that the remodeling pacing should not be adjusted, No in Block 204, the processor 80 may determine whether to monitor an additional long-term parameter, Block 208, to determine whether the additional long-term parameter indicates that the remodeling pacing has resulted in there being successful normalization of the patient's heart.

If an additional long-term parameter is not to be determined, No in Block 208, the processor 80 waits for the next scheduled time to perform long-term monitoring of the remodeling pacing, Yes in Block 200. If an additional long-term parameter is to be determined, Yes in Block 208, the processor 80 monitors the additional long-term parameter, Block 202, to determine whether the additional long-term parameter indicates that the remodeling pacing has resulted in there being successful normalization of the patient's heart. A determination is then made, based on the additional long-term parameter, as to whether to adjust the remodeling pacing, Block 204. If the processor 80 determines that the additional long-term parameter indicates that the remodeling pacing should be adjusted, Yes in Block 204, the processor 80 adjusts the remodeling pacing, Block 206, and waits for the next scheduled time to perform long-term monitoring of the remodeling pacing, Yes in Block 200. On the other hand, if the processor 80 determines that the additional long-term parameter indicates that the remodeling pacing should not be adjusted, No in Block 204, the processor 80 may determine whether to monitor an additional long-term parameter, Block 208.

In this way, in one example, the processor 80 may monitor a single long-term parameter to determine whether the long-term parameter indicates that the remodeling pacing should be adjusted. In another example, the processor 80 may monitor multiple long-term parameters to determine whether at least one of the long-term parameters indicates that the remodeling pacing should be adjusted.

According to one example, the processor 80 may monitor a QRS duration of the patient, Block 202, to determine whether the QRS duration is increasing over time as a result of the delivered remodeling pacing. If the QRS duration is determined to be increasing, the processor 80 determines the remodeling pacing should be adjusted, Yes in Block 204, and therefore makes the adjustment, Block 206, by reducing the rate and or duration of the delivered remodeling pacing and waits for the next scheduled time to perform long-term monitoring of the remodeling pacing, Yes in Block 200. On the other hand, if the QRS duration is not determined to be increasing the processor 80 determines that the remodeling pacing should not be adjusted, No in Block 204.

In another example, the processor 80 may monitor one or more circadian parameters, Block 202, to determine whether to adjust the period of time during which the remodeling pacing is to be delivered. For example, assuming the processor 80 delivers the remodeling pacing during a predetermined time of day when the patient is most likely to inactive, such as between the hours of 12 A.M.-5 A.M., as described above, the processor 80 may divide the period of time during which the remodeling pacing is to be delivered into predetermined time segments, such as 20 minute time segments for example, and determine for each of the 20 minute time segments, or for a predetermined number of beats during the segment, whether there is a lack of conduction from the atria to the ventricles indicative of AV-block occurring for that 20 minute time segment. The processor 80 then adjusts the time period for delivery of the remodeling pacing, Block 204, by not delivering the remodeling pacing during those 20-minute time segments of the initial delivery period, i.e., between the hours of 12 A.M.-5 A.M., for which AV-block is determined to likely occur.

In addition to the previously described pacing algorithms, a pacemaker can use one or more pacing regimens to remodel the heart. In another example, the processor 80 may merely characterize the patient circadian rhythms throughout the day, deliver rapid pacing during those rhythms and determine when the patient's heart is likely to conduct in a more normal manner based on the delivered rapid pacing, indicating that AV-block is less likely. The processor 80 then adjusts the time period for delivery of the remodeling pacing, Block 204, by delivering the remodeling pacing during those periods when AV-block is less likely. In this way, the processor utilizes circadian parameters to learn or determine when to deliver the remodeling pacing rather than merely delivering the remodeling pacing during a fixed time period.

In another example, the processor 80 may monitor one or more long-term parameters, Block 202, to identify whether there is a threshold level of long-term improvement in cardiac normalization. For example, the processor 80 may determine there is a threshold level of long-term improvement if a slope of the cardiac output of the patient is increasing. If there is a threshold level of long-term improvement, the processor 80 may adjust the rate and/or duration of the remodeling pacing. In another example, the processor 80 may determine there is a threshold level of long-term improvement if there is a desired change in pulmonary artery pressure, or a desired changed in impedance, such as a shift in impedance indicative of dilation of chambers of the heart. If there is a threshold level of long-term improvement as a result of the delivered remodeling pacing, the processor 80 may increase the rate and/or duration of the delivered remodeling pacing, Block 206.

In another example, the processor 80 may be programmed to utilize a predetermined duty cycle range for delivery of the remodeling pacing, such as a range between a minimum time period of 4 hours per day and a maximum time period of 8 hours per day. In this way, if there is a threshold level of long-term improvement as a result of the delivered remodeling pacing, the processor 80 may increase the duration of the delivered remodeling pacing, Block 206, unless the maximum duty cycle has been reached. Once the maximum duty cycle has been reached, the processor 80 may maintain delivery of the remodeling pacing at the maximum duty cycle.

Figure 8:
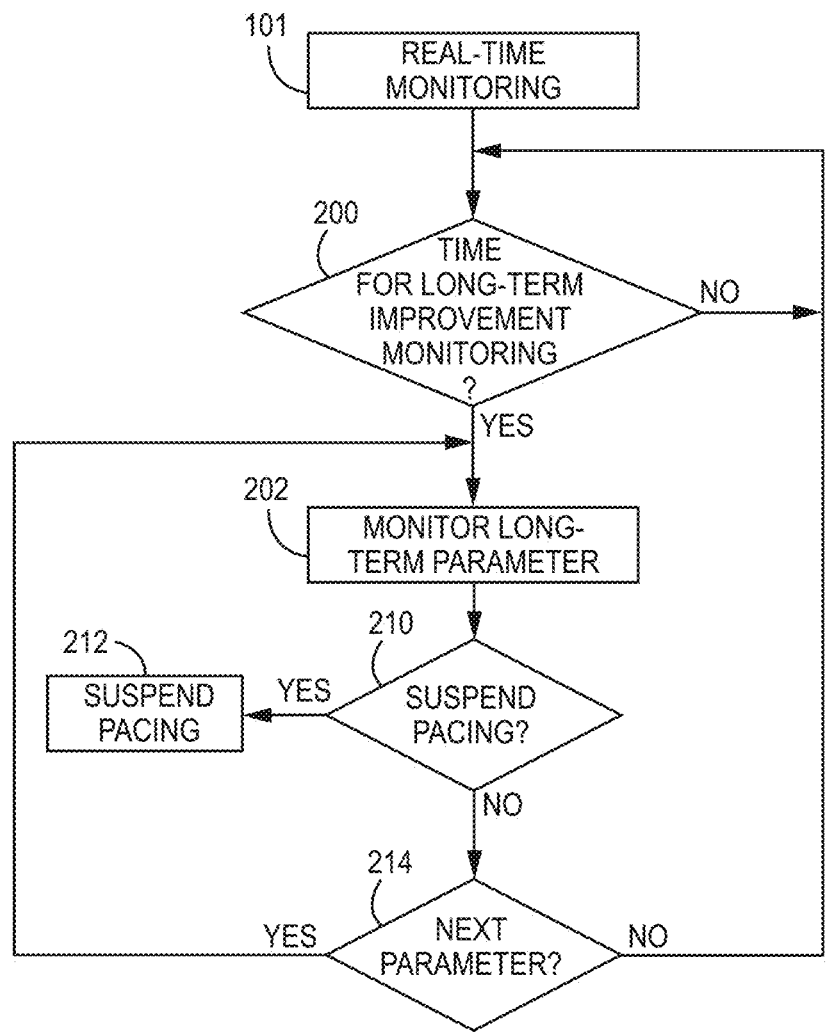
FIG. 8 is a flowchart of a method of delivering a pacing therapy for cardiac remodeling according to an example of the present disclosure.

FIG. 8 is a flowchart of a method of delivering a pacing therapy for cardiac remodeling according to an example of the present disclosure. According to another example, once the processor 80 determines that it is time to perform long-term monitoring of the remodeling pacing, Yes in Block 200, the processor 80 begins monitoring one or more long-term parameters associated with long-term delivery of the remodeling pacing, Block 202, and evaluates long-term effects of the delivered remodeling pacing to determine whether the remodeling pacing should be suspended.

As illustrated in FIG. 8, the monitoring of a long-term parameter, Block 202, may include the processor 80 monitoring a parameter to determine whether to either suspend delivery of the remodeling pacing, Yes in Block 210, or to maintain delivery of the remodeling pacing at the current set rate and/or duration, No in Block 210. For example, the monitoring of a long-term parameter, Block 202, may include monitoring a return to resting heart rate of the patient over an extended period of time to determine whether there is a change in the patient's long-term resting heart rate.

For example, the processor 80 may determine a recovery rate associated with the amount of time for the heart rate to return to a resting heart rate after delivery of the remodeling pacing at an elevated heart rate resulting during the delivered remodeling pacing. The determined recovery rate is compared to a baseline recovery rate, determined at implant for example. If there is not a reduction in the amount of time associated with the determined recovery rate over a long-term period of time, such as one week for example, the processor 80 determines that the long-term parameter indicates that the remodeling pacing should not be suspended, No in Block 210, and therefore delivery of the remodeling pacing is continued or maintained at the current rate and/or duration. If there is a reduction in the amount of time associated with the determined recovery rate, the processor 80 determines that the remodeling pacing has resulted in a desired level of normalization of the condition of patient's heart, and therefore delivery of the remodeling pacing should be suspended, Yes in Block 210, and therefore suspends delivery of the remodeling pacing, Block 212.

In another example, if the processor 80 determines that the long-term parameter indicates that the remodeling pacing should not be suspended, No in Block 210, based on the determined recovery rate and therefore delivery of the remodeling pacing is continued or maintained at the current rate and/or duration, the processor 80 may determine whether to monitor an additional long-term parameter, Block 214, to determine whether the additional long-term parameter indicates that the remodeling pacing should be suspended.

In another example, the monitoring of a long-term parameter, Block 202, may include monitoring a systolic time interval (STI) over an extended period of time to determine whether there is a change in the patient's long-term STI. The current long-term STI is compared to a baseline STI, determined at implant for example. If there is not a predetermined reduction in the STI, such as a 30 percent reduction for example, the processor 80 determines that the long-term parameter indicates that the remodeling pacing should not be suspended, No in Block 210, and therefore delivery of the remodeling pacing is continued or maintained at the current rate and/or duration. If there is a predetermined reduction in the current determined STI, the processor 80 determines that the remodeling pacing has resulted in a desired level of normalization of the condition of patient's heart, and therefore delivery of the remodeling pacing should be suspended, Yes in Block 210, and therefore suspends delivery of the remodeling pacing, Block 212.

In another example, if the processor 80 determines that the long-term parameter indicates that the remodeling pacing should not be suspended, No in Block 210, based on the determined reduction in the STI and therefore delivery of the remodeling pacing is continued or maintained at the current rate and/or duration, the processor 80 may determine whether to monitor an additional long-term parameter, Block 214, to determine whether the additional long-term parameter indicates that the remodeling pacing should be suspended.

In another example, the monitoring of a long-term parameter, Block 202, may include monitoring a biomarker indicator for diagnosing congestive heart failure (CHF), such as brain natriuretic peptide (BNP) for example, over an extended period of time to determine whether there is a change in the biomarker that would indicate the delivered remodeling pacing has resulted in a desired level of normalization of the condition of the patient's heart. The biomarker measured over a long period of time is compared to a baseline measure, determined at implant for example. If there is not a predetermined long-term change in the biomarker, the processor 80 determines that the long-term parameter indicates that the remodeling pacing should not be suspended, No in Block 210, and therefore delivery of the remodeling pacing is continued or maintained at the current rate and/or duration. If there is a predetermined long-term change in the biomarker, the processor 80 determines that the remodeling pacing has resulted in a desired level of normalization of the condition of patient's heart, and therefore delivery of the remodeling pacing should be suspended, Yes in Block 210, and thus suspends delivery of the remodeling pacing, Block 212.

In another example, if the processor 80 determines that the long-term parameter indicates that the remodeling pacing should not be suspended, No in Block 210, based on the determined reduction in the STI and therefore delivery of the remodeling pacing is continued or maintained at the current rate and/or duration, the processor 80 may determine whether to monitor an additional long-term parameter, Block 214, to determine whether the additional long-term parameter indicates that the remodeling pacing should be suspended.

Figure 9:
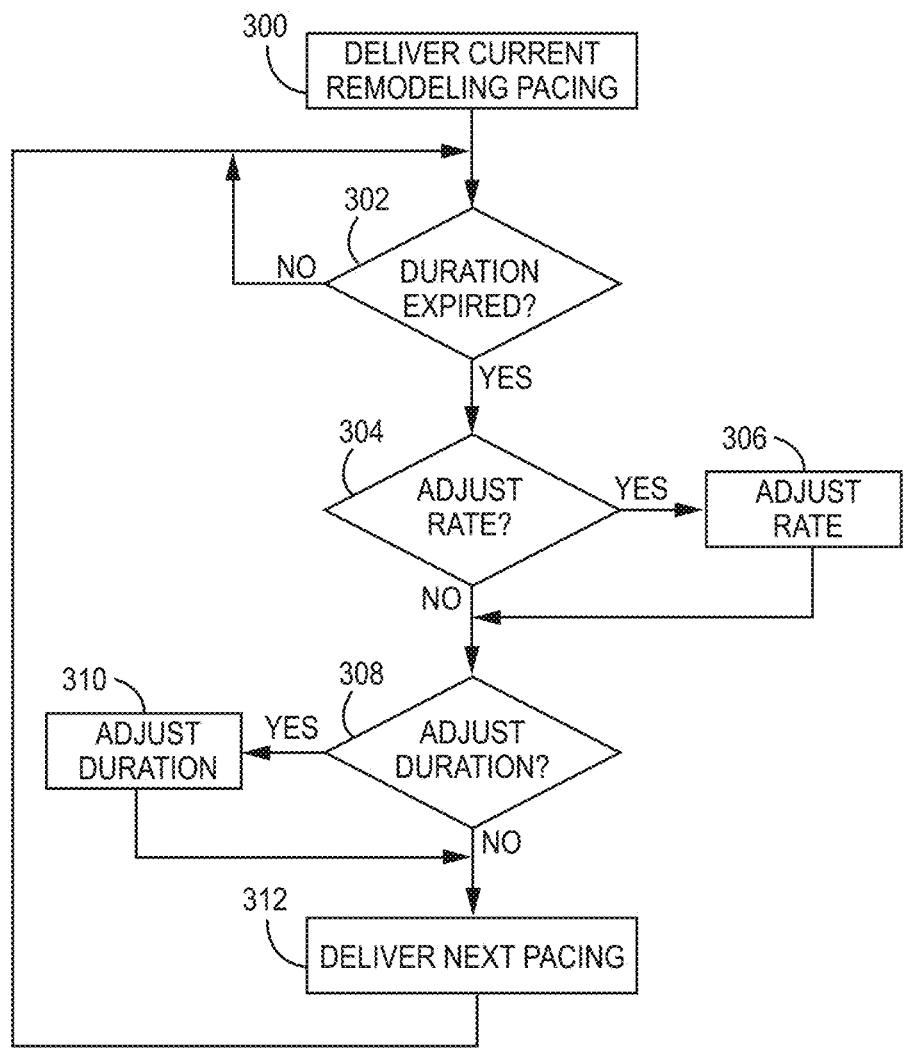
FIG. 9 is a flowchart of a method of delivering a remodeling pacing therapy according to an example of the present disclosure.

FIG. 9 is a flowchart of a method of delivering a remodeling pacing therapy according to an example of the present disclosure. As illustrated in FIG. 9, in order to increase the likelihood that the delivery of the remodeling pacing will be effective in causing a desired level of normalization of the condition of patient's heart, the processor 80 may deliver the remodeling pacing during multiple intervals, with the multiple intervals having variations in the rate and/or duration of the remodeling pacing in such a way as to increase muscular endurance of the heart. For example, the processor 80 may deliver the remodeling pacing at the current set rate, Block 300, for a predetermined duration, and once the remodeling pacing has been delivered at the current rate for the current duration, Yes in Block 302, determine whether to adjust the rate from the current rate to a next rate, Block 304, and/or determine whether to adjust the duration from the current duration to a next duration, Block 308.

In this way, once the remodeling pacing has been delivered at the current rate for the current duration, Yes in Block 302, the processor 80 either adjusts only the rate, Block 306, and delivers the next remodeling pacing interval, Block 312, with the adjusted rate for the current duration, adjusts only the duration, Block 310, and delivers the next remodeling pacing interval, Block 312, at the current rate with the adjusted next duration, adjusts both the current rate, Block 306, and the current duration, Block 310, and delivers the next remodeling pacing interval, Block 312, at the adjusted rate for the adjusted duration, or makes no adjustment to the rate or the duration and continues delivering the next remodeling pacing interval, Block 312, at the current rate for the current duration. Once the duration has expired during delivery of the next remodeling pacing, Yes in Block 302, the process is repeated to generate a next remodeling pacing delivery interval until the current remodeling pacing delivery session has ended.

In this way, the processor 80 may deliver remodeling pacing during a first interval having a first rate and a first duration, determine whether to adjust one or both of the first rate and the first duration during delivery of remodeling pacing during a next interval subsequent to the first interval, and deliver remodeling pacing during the next interval in response to the determining, so that the next interval may include the remodeling pacing being delivered having one of both the first rate and the first duration, the adjusted rate and the first duration, the first rate and the adjusted duration, and both the adjusted rate and the adjusted duration.

In particular, in one example delivery of the remodeling pacing may include a warm-up interval during which the remodeling pacing is delivered for an initial duration at a rate slightly above a resting heart rate associated with the patient, followed by a build-up interval during which the remodeling pacing is delivered at an increased rate for a shorter duration relative to the initial duration. Once delivery of the remodeling pacing during the build-up interval is completed, the remodeling pacing may be delivered using the rate and duration of the initial interval to generate an up/down delivery of the remodeling pacing, or may be delivered at an increased rate, increased duration, or an increased rate and duration, etc. In this way, the remodeling pacing may be delivered in repeatedly ascending and/or descending patterns to increase muscular endurance and thereby increase the likelihood that the delivery of the remodeling pacing will be effective in causing a desired level of normalization of the condition of patient's heart.

In one example, delivery of the remodeling pacing may include a 10-minute warm-up interval (first time period) during which the remodeling pacing is delivered at a low rate just above the patient's resting rate (a first rate to increase the heart rate up to 30 heart beats per minute (HBM) above resting heart rate), followed by a 3 minute first build-up interval during which the remodeling pacing is delivered at a maximum rate (such as up to 50 HBM above the first heart rate), followed by a second interval (e.g., 2 minute interval) during which the remodeling pacing is delivered at a rate less than the maximum rate, followed by a third build-up interval (e.g., 2 minute interval) during which the remodeling pacing is delivered at the maximum rate, followed by a one minute time interval during which the remodeling pacing is delivered at the rate less than the maximum rate, followed by a one minute interval during which the remodeling pacing is delivered at the maximum rate, followed by a 1 minute time interval during which the remodeling pacing is delivered at the rate less than the maximum rate. The process may then be repeated. For example, this algorithm may be repeatedly implemented up to 1 hour per day.

In another example, delivery of the remodeling pacing may include delivery at the same rate but at varying duration. For example, delivery of the remodeling pacing may include delivering the remodeling pacing during a two minute interval (first interval) at a given rate (first rate), followed by delivering the remodeling pacing during a four minute interval (second interval) at the same rate, followed by delivering the remodeling pacing during a six minute interval (third interval) at the same rate, followed by delivering the remodeling pacing during another six minute interval (fourth interval) at the same rate, followed by delivering the remodeling pacing during a four minute interval (fifth interval) at the same rate, and followed by delivering the remodeling pacing during a two minute interval (sixth interval) at the same rate. In another example, the delivery may include a recovery interval (seventh interval) between each of the varying intervals during which the remodeling pacing is delivered at a reduced rate and reduced duration. This algorithm may be repeatedly implemented up to 1 hour per day.

In another example, the remodeling pacing may be delivered in a stepped pattern that includes a warm-up interval (first interval that allows the heart rate to gradually build up to 20 HBM) during which the remodeling pacing is delivered at a minimum rate (e.g. raises heart rate by up to 30 HBM), followed by a build-up interval during which the remodeling pacing is delivered at a first rate greater than the minimum rate delivered during the warm-up interval, followed by another build-up interval during which the remodeling pacing is delivered a second rate greater than the minimum rate (e.g. increases heart rate up to 30HBM above the first rate) and either equal to or greater than the first rate utilized during the previous build-up interval. This algorithm may be repeatedly implemented up to 1 hour per day.

In another example, delivery of the remodeling pacing may include an initial interval (up to 3 to 5 minutes) during which the remodeling pacing is delivered at a high rate (causing the heart rate to increase up to 50 HBM), followed by a next interval during which the remodeling pacing is delivered at a reduced rate (decrease HBM by 20 HBM from first interval), or an initial interval during which the remodeling pacing is delivered at a reduced rate, followed by a next interval during which the remodeling pacing is delivered at a high rate, may include alternating between the two.

In this way, delivery of the remodeling pacing may include multiple combinations of different rate and/or duration patterns being delivered over long or short periods of time, such as days or one or more weeks. In addition, recovery intervals may also be included during which delivery of the remodeling pacing is either withheld for a period of time or is delivered at a reduced rate and/or duration to allow variable patterns for delivery of the remodeling pacing, which may also include a combination of one or more a warm-up intervals and one or more build-up intervals, resulting in a desired level of normalization of the condition of patient's heart.

The techniques described in this disclosure, including those attributed to the IMD 16, the programmer 24, the processor 80 or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

In one example, the exercise regimens described herein are performed while the patient's is sleeping however, the exercise regimens can be performed without detection of any patient data (e.g., detection of inactivity). Additionally, the exercise regimens are not used for diagnostic purposes; rather, exercising the heart is for the purpose of remodeling the heart.

Illustrative Embodiments

Embodiment 1: A method comprising:
  delivering cardiac remodeling pacing to stimulate normalization of a condition of the patient's heart;
  monitoring one or more parameters in response to the delivered remodeling pacing;
  determining whether the cardiac remodeling pacing has an effect on cardiac normalization in response to the monitoring; and
  adjusting the cardiac remodeling pacing in response to the determined effect on cardiac normalization.

Embodiment 2: A cardiac device for delivering a cardiac remodeling pacing to a patient, comprising:
  a housing;
  a plurality of electrodes electrically connected to the housing to deliver the cardiac remodeling pacing to stimulate normalization of a condition of the patient's heart; and
  a processor positioned within the housing and configured to:
    determine one or more parameters in response to the delivered cardiac remodeling pacing,
    determine whether the cardiac remodeling pacing has an effect on cardiac normalization in response to the monitoring, and
    adjust the cardiac remodeling pacing in response to the determined effect on cardiac normalization.

Embodiment 3: The method or device as set forth in any one of embodiments 1-2, wherein determining whether the cardiac remodeling pacing has an effect on cardiac normalization in response to the monitoring comprises:
  determining tissue perfusion during delivery of the remodeling pacing therapy;
  comparing the determined tissue perfusion with a non-paced baseline tissue perfusion level determined prior to the cardiac remodeling pacing being delivered to the patient,
  wherein determining whether the cardiac remodeling pacing has an effect on cardiac normalization in response to the monitoring comprises determining whether the cardiac remodeling pacing has had an effect on cardiac normalization in response to the comparing.

Embodiment 4: The method or device as set forth in embodiment 3, wherein comparing the determined tissue perfusion with a non-paced baseline tissue perfusion level determined prior to the cardiac remodeling pacing being delivered to the patient comprises determining whether there is an increase in tissue perfusion relative to the baseline tissue perfusion level,
  wherein determining whether the cardiac remodeling pacing has had an effect on cardiac normalization in response to the comparing comprises determining the cardiac remodeling pacing has had an effect on cardiac normalization in response to there being an increase in tissue perfusion relative to the baseline tissue perfusion level, and
  wherein adjusting the cardiac remodeling pacing in response to the determined effect on cardiac normalization comprises adjusting the cardiac remodeling pacing in response to determining an increase in tissue perfusion.

Embodiment 5: The method or device as set forth in embodiment 4, wherein determining the cardiac remodeling pacing has had an effect on cardiac normalization in response to there being an increase in tissue perfusion relative to the baseline tissue perfusion level comprises determining whether a slope of a cardiac output signal is increasing, and
  wherein adjusting the cardiac remodeling pacing in response to determining an increase in tissue perfusion comprises adjusting the cardiac remodeling pacing in response to determining that the slope of the cardiac output signal is increasing.

Embodiment 6: The method or device as set forth in any one of embodiments 1-5, wherein determining whether the cardiac remodeling pacing has an effect on cardiac normalization in response to the monitoring comprises determining whether the effect on cardiac normalization is greater than a symptom avoidance threshold, and wherein adjusting the cardiac remodeling pacing in response to the determined effect on cardiac normalization comprises adjusting the cardiac remodeling pacing in response to the effect on cardiac normalization being greater than the symptom avoidance threshold.

Embodiment 7: The method or device as set forth in embodiment 6, wherein determining whether the effect on cardiac normalization is greater than a symptom avoidance threshold comprises:

determining whether there has been an increase in premature ventricular contractions (PVCs) occurring during the delivery of the cardiac remodeling pacing; and determining the effect on cardiac normalization is greater than the symptom avoidance threshold in response to an increase in PVCs.

Embodiment 8: The method or device as set forth in embodiments 6-7, wherein determining whether the effect on cardiac normalization is greater than a symptom avoidance threshold comprises:

sensing a heart sounds signal during delivery of the cardiac remodeling pacing; and determining the effect on cardiac normalization is greater than the symptom avoidance threshold in response one of a decrease in amplitudes of S1 and S2 heart sounds and an S3 heart sound being sensed in response to the sensed heart sounds signal.

Embodiment 9: The method or device as set forth in embodiments 6-8, wherein determining whether the effect on cardiac normalization is greater than a symptom avoidance threshold comprises:

determining whether an increase of a biomarker indicator is greater than a threshold indicative of heart failure during the delivery of the cardiac remodeling pacing; and determining the effect on cardiac normalization is greater than the symptom avoidance threshold in response to the increase of the biomarker indicator being greater than the threshold indicative of heart failure.

Embodiment 10: The method or device as set forth in embodiment 9, wherein the biomarker indicator comprises a brain natriuretic peptide.

Embodiment 11: The method or device as set forth in embodiments 6-10, wherein monitoring one or more parameters in response to the delivered remodeling pacing comprises sensing a cardiac signal, and wherein determining whether the effect on cardiac normalization is greater than a symptom avoidance threshold comprises:

determining whether there has been an increase in ST segment measurements of the sensed cardiac signal during the delivery of the cardiac remodeling pacing; and determining the effect on cardiac normalization is greater than the symptom avoidance threshold in response to there being an increase in ST segment measurements.

Embodiment 12: The method or device as set forth in any one of embodiments 1-11, wherein the one or more parameters comprise tissue perfusion, atrial perfusion, estimated pulmonary artery pressure (ePad), right ventricular pressure, left ventricular pressure, PVCs, ST segment measurements, a biomarker indicator, heart sounds, and impedance.

Embodiment 13: A method comprising:

delivering cardiac remodeling pacing to stimulate normalization of a condition of the patient's heart;

performing short-term monitoring of one or more parameters in response to the delivered cardiac remodeling pacing;

monitoring one or more long-term parameter indicative of a long-term effect of the delivered cardiac remodeling pacing on cardiac normalization;

determining the long-term effect of the delivered cardiac remodeling pacing on cardiac normalization in response to the monitoring; and adjusting the cardiac remodeling pacing in response to one or both of the short-term monitoring and the determined long-term effect on cardiac normalization.

Embodiment 14: A cardiac device for delivering a cardiac remodeling pacing to a patient, comprising:

a housing;

a plurality of electrodes electrically connected to the housing to deliver cardiac remodeling pacing to stimulate normalization of a condition of the patient's heart; and a processor positioned within the housing and configured to:

perform short-term monitoring of one or more parameters in response to the delivered cardiac remodeling pacing, monitor one or more long-term parameter indicative of a long-term effect of the delivered cardiac remodeling pacing on cardiac normalization, determine the long-term effect of the delivered cardiac remodeling pacing on cardiac normalization in response to the monitoring, and adjust the cardiac remodeling pacing in response to one or both of the short-term monitoring and the determined long-term effect on cardiac normalization.

Embodiment 15: The method or device as set forth in one of embodiments 13-14, wherein monitoring one or more long-term parameter indicative of a long-term effect of the delivered cardiac remodeling pacing on cardiac normalization comprises sensing a cardiac signal during delivery of the cardiac remodeling pacing, wherein determining the long-term effect of the delivered cardiac remodeling pacing on cardiac normalization in response to the monitoring comprises:

determining QRS durations over a predetermined long-term period of time in response to the sensed cardiac signal, and determining whether the QRS durations are increasing; and wherein adjusting the cardiac remodeling pacing in response to one or both of the short-term monitoring and the determined long-term effect on cardiac normalization comprises adjusting the cardiac remodeling pacing in response to the QRS durations in response to the QRS duration determined to be increasing.

Embodiment 16: The method or device as set forth in one of embodiments 13-15, wherein the method further comprises or the processor of the device is further configured to execute:

delivering the cardiac remodeling pacing during a predetermined time period; and dividing the period of time during which the cardiac remodeling pacing is delivered into predetermined time segments, wherein determining the long-term effect of the delivered cardiac remodeling pacing on cardiac normalization in response to the monitoring comprises determining, for each of the predetermined time segments, whether AV-block is occurring, and wherein adjusting the cardiac remodeling pacing in response to one or both of the short-term monitoring and the determined long-term effect on cardiac normalization comprises adjusting delivery of the cardiac remodeling pacing in response to the predetermined time segments for which AV-block is determined to occur.

Embodiment 17: The method or device as set forth in one of embodiments 13-16, wherein determining the long-term effect of the delivered cardiac remodeling pacing on cardiac normalization in response to the monitoring comprises:
determining whether a slope of a cardiac output signal is increasing; and
determining long-term improvement in cardiac normalization in response to determining that the slope of the cardiac output signal is increasing.

Embodiment 18: The method or device as set forth in one of embodiments 13-17, wherein monitoring one or more long-term parameter indicative of a long-term effect of the delivered cardiac remodeling pacing on cardiac normalization comprises sensing a cardiac signal during delivery of the cardiac remodeling pacing,
wherein determining the long-term effect of the delivered cardiac remodeling pacing on cardiac normalization in response to the monitoring comprises determining whether there is a predetermined change in impedance indicative of dilation of heart chambers in response to the sensed cardiac signal,
wherein adjusting the cardiac remodeling pacing in response to one or both of the short-term monitoring and the determined long-term effect on cardiac normalization comprises adjusting delivery of the cardiac remodeling pacing in response to the determined change in impedance.

Embodiment 19: The method or device as set forth in one of embodiments 13-18, wherein determining the long-term effect of the delivered cardiac remodeling pacing on cardiac normalization in response to the monitoring comprises determining changes in pulmonary pressure during long-term delivery of the cardiac remodeling pacing; and
wherein adjusting the cardiac remodeling pacing in response to one or both of the short-term monitoring and the determined long-term effect on cardiac normalization comprises adjusting delivery of the cardiac remodeling pacing in response to the determined changes in pulmonary pressure.

Embodiment 20: The method or device as set forth in one of embodiments 13-19, wherein adjusting the cardiac remodeling pacing in response to one or both of the short-term monitoring and the determined long-term effect on cardiac normalization comprises adjusting a duty cycle of the cardiac remodeling pacing in response to the determined long-term effect.

Embodiment 21: The method or device as set forth in one of embodiments 13-20, wherein determining the long-term effect of the delivered cardiac remodeling pacing on cardiac normalization in response to the monitoring comprises:
determining a recovery rate associated with an amount of time for a heart rate to return to a resting heart rate after delivery of the cardiac remodeling pacing; and
comparing the determined recovery rate to a baseline recovery rate,
wherein adjusting the cardiac remodeling pacing in response to one or both of the short-term monitoring and the determined long-term effect on cardiac normalization comprises determining whether to suspend delivery of the cardiac remodeling pacing in response to the comparing.

Embodiment 22: The method or device as set forth in one of embodiments 13-21, wherein monitoring one or more long-term parameter indicative of a long-term effect of the delivered cardiac remodeling pacing on cardiac normalization comprises sensing a cardiac signal during delivery of the cardiac remodeling pacing,
wherein determining the long-term effect of the delivered cardiac remodeling pacing on cardiac normalization in response to the monitoring comprises determining whether there is a predetermined change in a systolic time interval in response to the sensed cardiac signal, and
wherein adjusting the cardiac remodeling pacing in response to one or both of the short-term monitoring and the determined long-term effect on cardiac normalization comprises determining whether to suspend delivery of the cardiac remodeling pacing in response to the determined change in the systolic time interval.

Embodiment 23: The method or device as set forth in one of embodiments 13-22, wherein determining the long-term effect of the delivered cardiac remodeling pacing on cardiac normalization in response to the monitoring comprises:
determining a long-term change in a biomarker indicator indicative of heart failure during the delivery of the cardiac remodeling pacing;
determining whether the long-term change in the biomarker indicator is indicative of there being a long-term effect on cardiac normalization; and
wherein adjusting the cardiac remodeling pacing in response to one or both of the short-term monitoring and the determined long-term effect on cardiac normalization comprises suspending delivery of the cardiac remodeling pacing in response to the long-term change in the biomarker indicator being indicative of there being a long-term effect on cardiac normalization.

Embodiment 24: The method or device as set forth in embodiment 23, wherein the biomarker indicator comprises a brain natriuretic peptide.

Embodiment 25: The method or device as set forth in one of embodiments 13-24, wherein monitoring one or more long-term parameter indicative of a long-term effect of the delivered cardiac remodeling pacing on cardiac normalization comprises monitoring a systolic time interval (STI) over an extended period of time to generate a long-term STI,
wherein determining the long-term effect of the delivered cardiac remodeling pacing on cardiac normalization in response to the monitoring comprises comparing the long-term STI to a baseline STI,
wherein adjusting the cardiac remodeling pacing in response to one or both of the short-term monitoring and the determined long-term effect on cardiac normalization comprises determining whether to suspend delivery of the cardiac remodeling pacing in response to the comparing.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:
1. A cardiac device for delivering a cardiac remodeling pacing therapy to a patient, the device comprising:
a housing;
a plurality of electrodes electrically connected to the housing configured to deliver the cardiac remodeling pacing therapy; and a processor positioned within the housing and configured to deliver the cardiac remodeling pacing therapy using the plurality of electrodes to dilate the left ventricular (LV) chamber of the patient's heart over time to stimulate a cardiac normalization of a condition of the patient's heart, monitor one or more parameters including tissue perfusion in response to the delivered cardiac remodeling pacing therapy, determine whether the cardiac remodeling pacing therapy has an effect on the cardiac normalization in response to the monitoring, and adjust the cardiac remodeling pacing therapy in response to the determined effect on the cardiac normalization.

2. The device of claim 1, wherein the processor is further configured to:
compare the monitored tissue perfusion with a non-paced baseline tissue perfusion level monitored prior to the cardiac remodeling pacing therapy being delivered to the patient; and
determine whether the cardiac remodeling pacing therapy has had an effect on the cardiac normalization in response to the comparing.

3. The device of claim 2, wherein the processor is configured to:
compare the monitored tissue perfusion with a non-paced baseline tissue perfusion level monitored prior to the cardiac remodeling pacing therapy being delivered to the patient by determining whether there is an increase in tissue perfusion relative to the non-paced baseline tissue perfusion level,
determine whether the cardiac remodeling pacing therapy has had an effect on the cardiac normalization in response to the comparing by determining the cardiac remodeling pacing therapy has had an effect on the cardiac normalization in response to there being an increase in tissue perfusion relative to the non-paced baseline tissue perfusion level, and
adjust the cardiac remodeling pacing therapy in response to the determined effect on the cardiac normalization by adjusting the cardiac remodeling pacing therapy in response to determining an increase in tissue perfusion.

4. The device of claim 3, wherein the processor is configured to:
determine the cardiac remodeling pacing therapy has had an effect on the cardiac normalization in response to there being an increase in the tissue perfusion relative to the non-paced baseline tissue perfusion level by determining whether a slope of a cardiac output signal is increasing, and
adjust the cardiac remodeling pacing therapy in response to determining an increase in tissue perfusion by adjusting the cardiac remodeling pacing therapy in response to determining that the slope of the cardiac output signal is increasing.

5. The device of claim 1, wherein the processor is configured to:
determine whether the cardiac remodeling pacing therapy has an effect on the cardiac normalization in response to the monitoring by determining whether the effect on the cardiac normalization is greater than a symptom avoidance threshold, and
adjust the cardiac remodeling pacing therapy in response to the determined effect on the cardiac normalization by adjusting the cardiac remodeling pacing therapy in response to the effect on the cardiac normalization being greater than the symptom avoidance threshold.

6. The device of claim 5, wherein the processor is configured to: determine whether the effect on the cardiac normalization is greater than the symptom avoidance threshold by:
determining whether there has been an increase in premature ventricular contractions (PVCs) occurring during the delivery of the cardiac remodeling pacing therapy; and
determining the effect on the cardiac normalization is greater than the symptom avoidance threshold in response to an increase in PVCs.

7. The device of claim 5, wherein the processor is configured to:
monitor one or more parameters in response to the delivered remodeling pacing therapy by sensing a heart sounds signal during the delivery of the cardiac remodeling pacing therapy, and
determine whether the effect on the cardiac normalization is greater than the symptom avoidance threshold by determining the effect on the cardiac normalization is greater than the symptom avoidance threshold in response to a decrease in amplitudes of S1 and S2 heart sounds or an S3 heart sound being sensed in response to the sensed heart sounds signal.

8. The device of claim 5, wherein the processor is configured to: determine whether the effect on the cardiac normalization is greater than the symptom avoidance threshold by:
determining whether an increase of a biomarker indicator is greater than a threshold indicative of congestive heart failure during the delivery of the cardiac remodeling pacing therapy; and
determining the effect on the cardiac normalization is greater than the symptom avoidance threshold in response to the increase of the biomarker indicator being greater than the threshold indicative of heart failure.

9. The device of claim 8, wherein the biomarker indicator comprises a brain natriuretic peptide.

10. The device of claim 5, wherein the processor is configured to:
monitor one or more parameters in response to the delivered remodeling pacing therapy by sensing a cardiac signal, and
wherein the processor is configured to determine whether the effect on the cardiac normalization is greater than the symptom avoidance threshold by:
determining whether there has been an increase in ST segment measurements of the sensed cardiac signal during the delivery of the cardiac remodeling pacing therapy; and
determining the effect on the cardiac normalization is greater than the symptom avoidance threshold in response to there being an increase in ST segment measurements.

11. The device of claim 1, wherein the one or more parameters further comprise estimated pulmonary artery pressure (ePad), right ventricular pressure, left ventricular pressure, PVCs, ST segment measurements, a biomarker indicator, heart sounds, or impedance.

12. A cardiac device for delivering a cardiac remodeling pacing therapy to a patient comprising:
a housing;
a plurality of electrodes electrically connected to the housing configured to deliver the cardiac remodeling pacing therapy; and a processor positioned within the housing and configured to:
  deliver the cardiac remodeling pacing therapy using the plurality of electrodes to dilate the left ventricular (LV) chamber of the patient's heart over time to stimulate a cardiac normalization of a condition of the patient's heart,
  monitor one or more parameters in response to the delivered cardiac remodeling pacing therapy,
  determine whether the cardiac remodeling pacing therapy has an effect on the cardiac normalization by determining whether the effect on the cardiac normalization is greater than a symptom avoidance threshold in response to the monitoring, wherein the determining whether the effect on the cardiac normalization is greater than the symptom avoidance threshold by:
    determining whether there has been an increase in premature ventricular contractions (PVCs) occurring during the delivery of the cardiac remodeling pacing therapy;
    determining the effect on the cardiac normalization is greater than the symptom avoidance threshold in response to an increase in PVC; and
  adjust the cardiac remodeling pacing therapy in response to the determined effect on the cardiac normalization by adjusting the cardiac remodeling pacing therapy in response to the effect on the cardiac normalization being greater than the symptom avoidance threshold.

13. A cardiac device for delivering a cardiac remodeling pacing therapy to a patient comprising:
  a housing;
  a plurality of electrodes electrically connected to the housing configured to deliver the cardiac remodeling pacing therapy; and
  a processor positioned within the housing and configured to:
    deliver the cardiac remodeling pacing therapy using the plurality of electrodes to dilate the left ventricular (LV) chamber of the patient's heart over time to stimulate a cardiac normalization of a condition of the patient's heart,
    monitor one or more parameters in response to the delivered cardiac remodeling pacing therapy,
    determine whether the cardiac remodeling pacing therapy has an effect on the cardiac normalization by determining whether the effect on the cardiac normalization is greater than a symptom avoidance threshold in response to the monitoring, wherein the determining whether the effect on the cardiac normalization is greater than the symptom avoidance threshold by:
      sensing a heart sounds signal during the delivery of the cardiac remodeling pacing therapy;
      determining whether there has been a decrease in amplitudes of S1 and S2 heart sounds or an S3 heart sound being sensed in response to the sensed heart sounds signal;
      determining the effect on the cardiac normalization is greater than the symptom avoidance threshold in response to a decrease in amplitudes of S1 and S2 heart sounds or an S3 heart sound being sensed in response to the sensed heart sounds signal; and
    adjust the cardiac remodeling pacing therapy in response to the determined effect on the cardiac normalization by adjusting the cardiac remodeling pacing therapy in response to the effect on the cardiac normalization being greater than the symptom avoidance threshold.

14. A cardiac device for delivering a cardiac remodeling pacing therapy to a patient comprising:
  a housing;
  a plurality of electrodes electrically connected to the housing configured to deliver the cardiac remodeling pacing therapy; and
  a processor positioned within the housing and configured to:
    deliver the cardiac remodeling pacing therapy using the plurality of electrodes to dilate the left ventricular (LV) chamber of the patient's heart over time to stimulate a cardiac normalization of a condition of the patient's heart,
    monitor one or more parameters in response to the delivered cardiac remodeling pacing therapy,
    determine whether the cardiac remodeling pacing therapy has an effect on the cardiac normalization by determining whether the effect on the cardiac normalization is greater than a symptom avoidance threshold in response to the monitoring, wherein the determining whether the effect on the cardiac normalization is greater than the symptom avoidance threshold by:
      determining whether an increase of a biomarker indicator is greater than a threshold indicative of congestive heart failure during the delivery of the cardiac remodeling pacing therapy;
      determining the effect on the cardiac normalization is greater than the symptom avoidance threshold in response to the increase of the biomarker indicator being greater than the threshold indicative of heart failure; and
    adjust the cardiac remodeling pacing therapy in response to the determined effect on the cardiac normalization by adjusting the cardiac remodeling pacing therapy in response to the effect on the cardiac normalization being greater than the symptom avoidance threshold.

15. The device of claim 14, wherein the biomarker indicator comprises a brain natriuretic peptide.

16. A cardiac device for delivering a cardiac remodeling pacing therapy to a patient comprising:
  a housing;
  a plurality of electrodes electrically connected to the housing configured to deliver the cardiac remodeling pacing therapy; and
  a processor positioned within the housing and configured to:
    deliver the cardiac remodeling pacing therapy using the plurality of electrodes to dilate the left ventricular (LV) chamber of the patient's heart over time to stimulate a cardiac normalization of a condition of the patient's heart,
    monitor one or more parameters in response to the delivered cardiac remodeling pacing therapy,
    determine whether the cardiac remodeling pacing therapy has an effect on the cardiac normalization by determining whether the effect on the cardiac normalization is greater than a symptom avoidance threshold in response to the monitoring, wherein the determining whether the effect on the cardiac normalization is greater than the symptom avoidance threshold by:

determining whether there has been an increase in ST segment measurements of the sensed cardiac signal during the delivery of the cardiac remodeling pacing therapy;
determining the effect on the cardiac normalization is greater than the symptom avoidance threshold in response to there being an increase in the ST segment measurements; and
adjust the cardiac remodeling pacing therapy in response to the determined effect on the cardiac normalization by adjusting the cardiac remodeling pacing therapy in response to the effect on the cardiac normalization being greater than the symptom avoidance threshold.

* * * * *